US012611117B2

(12) United States Patent
    Eckerbom et al.

(10) Patent No.: US 12,611,117 B2
(45) Date of Patent: Apr. 28, 2026

(54) NASAL/ORAL CANNULA SYSTEM AND MANUFACTURING

(71) Applicant: Masimo Sweden AB, Danderyd (SE)

(72) Inventors: Anders Eckerbom, Danderyd (SE);
    Robert Zyzanski, Danderyd (SE)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/676,369

(22) Filed: May 28, 2024

(65) Prior Publication Data

US 2024/0306938 A1      Sep. 19, 2024

Related U.S. Application Data

(63) Continuation of application No. 16/601,326, filed on Oct. 14, 2019, now Pat. No. 12,036,014, which is a
(Continued)

(51) Int. Cl.
    B32B 41/00        (2006.01)
    A61B 5/097        (2006.01)
    (Continued)

(52) U.S. Cl.
    CPC ......... A61B 5/097 (2013.01); A61M 16/0666 (2013.01); A61M 16/0672 (2014.02);
    (Continued)

(58) Field of Classification Search
    CPC .............. A61B 5/097; A61B 2562/12; A61M 16/0666; A61M 16/0672; A61M 16/085;
    (Continued)

(56) References Cited

U.S. PATENT DOCUMENTS 4,960,128  A     10/1990  Gordon et al.
4,964,408  A     10/1990  Hink et al.
                 (Continued)

FOREIGN PATENT DOCUMENTS

EP       1 800 707      6/2007
IL         201847      6/2010
                 (Continued)

OTHER PUBLICATIONS

US 2022/0192529 A1, 06/2022, Al-Ali et al. (withdrawn)
                 (Continued)

*Primary Examiner* — Michael N Orlando
*Assistant Examiner* — Joshel Rivera
(74) *Attorney, Agent, or Firm* — Knobbe, Martens, Olson & Bear, LLP

(57) ABSTRACT

A nasal/oral cannula for collecting a flow of exhaled gases and its method of manufacture are disclosed. The cannula comprises an elongated tubular body having a first and a second end portion, a surface and an internal volume; a wall internally disposed within said tubular body, said wall defining a first subvolume of said internal volume in the lengthwise direction of the tubular body; and an inlet through said surface, for introducing exhaled gases into said first subvolume. The first end portion defines an exit port for exhaled gases from said subvolume, and said wall is arranged directly adjacent to said inlet.

20 Claims, 20 Drawing Sheets

Related U.S. Application Data continuation of application No. 15/004,695, filed on Jan. 22, 2016, now Pat. No. 10,441,196.

(60) Provisional application No. 62/107,232, filed on Jan. 23, 2015.

(51) Int. Cl.

| | | |
|---|---|---|
| *A61M 16/06* | (2006.01) | |
| *A61M 16/08* | (2006.01) | |
| *B29C 45/00* | (2006.01) | |
| *B29C 45/26* | (2006.01) | |
| *B29C 45/33* | (2006.01) | |
| *B29C 45/44* | (2006.01) | |
| *B29C 65/00* | (2006.01) | |
| *B29C 65/48* | (2006.01) | |
| *B29C 65/52* | (2006.01) | |
| *B29L 23/00* | (2006.01) | |

(52) U.S. Cl.
CPC ......... *A61M 16/085* (2014.02); *B29C 45/006* (2013.01); *B29C 45/261* (2013.01); *B29C 45/33* (2013.01); *B29C 45/44* (2013.01); *A61B 2562/12* (2013.01); *A61M 2230/432* (2013.01); *B29C 65/4895* (2013.01); *B29C 65/523* (2013.01); *B29C 66/1282* (2013.01); *B29C 66/1284* (2013.01); *B29C 66/52241* (2013.01); *B29L 2023/007* (2013.01)

(58) Field of Classification Search
CPC ........ A61M 2230/432; A61M 2207/10; A61M 25/0009; B29C 45/006; B29C 45/261; B29C 45/33; B29C 45/44; B29C 65/4895; B29C 65/523; B29C 66/1282; B29C 66/1284; B29C 66/52241; B29C 45/14065; B29L 2023/007; B29L 2031/7548
USPC .................... 156/60, 64, 350, 351, 378, 379
See application file for complete search history.

(56) References Cited

U.S. PATENT DOCUMENTS

| | | | |
|---|---|---|---|
| 4,989,599 | A | 2/1991 | Carter |
| 5,041,187 | A | 8/1991 | Hink et al. |
| 5,069,213 | A | 12/1991 | Hink et al. |
| 5,099,836 | A | 3/1992 | Rowland et al. |
| 5,137,017 | A | 8/1992 | Salter |
| 5,163,438 | A | 11/1992 | Gordon et al. |
| 5,319,355 | A | 6/1994 | Russek |
| 5,335,656 | A | 8/1994 | Bowe et al. |
| 5,337,744 | A | 8/1994 | Branigan |
| 5,341,805 | A | 8/1994 | Stavridi et al. |
| 5,377,676 | A | 1/1995 | Vari et al. |
| 5,431,170 | A | 7/1995 | Mathews |
| 5,436,499 | A | 7/1995 | Namavar et al. |
| 5,452,717 | A | 9/1995 | Branigan et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,685,299 | A | 11/1997 | Diab et al. |

| | | | |
|---|---|---|---|
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,857,461 | A | 1/1999 | Levitsky et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,010,937 | A | 1/2000 | Karam et al. |
| 6,011,986 | A | 1/2000 | Diab et al. |
| 6,027,452 | A | 2/2000 | Flaherty et al. |
| 6,036,642 | A | 3/2000 | Diab et al. |
| 6,040,578 | A | 3/2000 | Malin et al. |
| 6,045,509 | A | 4/2000 | Caro et al. |
| 6,066,204 | A | 5/2000 | Haven |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,115,673 | A | 9/2000 | Malin et al. |
| 6,124,597 | A | 9/2000 | Shehada et al. |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,373 | B1 | 6/2002 | Garside et al. |
| 6,415,167 | B1 | 7/2002 | Blank et al. |
| 6,422,240 | B1 | 7/2002 | Levitsky et al. |
| 6,430,437 | B1 | 8/2002 | Marro |
| 6,430,525 | B1 | 8/2002 | Weber et al. |

(56)                    References Cited

U.S. PATENT DOCUMENTS

| | | |
|---|---|---|
| 6,439,234 B1 | 8/2002 | Curti et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,215 B2 | 7/2003 | Wood |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,776,162 B2 | 8/2004 | Wood |
| 6,788,965 B2 | 9/2004 | Ruchti et al. |
| 6,792,300 B1 | 9/2004 | Diab et al. |
| 6,807,967 B2 | 10/2004 | Wood |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,986,353 B2 | 1/2006 | Wright |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,177 B2 | 2/2006 | Wood |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,059,328 B2 | 6/2006 | Wood |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,624 B2 | 3/2007 | Wood |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,318,437 B2 | 1/2008 | Gunaratnam et al. |
| 7,328,053 B1 | 2/2008 | Diab et al. |
| 7,332,784 B2 | 2/2008 | Mills et al. |
| 7,337,780 B2 | 3/2008 | Curti et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,383,839 B2 | 6/2008 | Porat et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |

(56)　　　References Cited

U.S. PATENT DOCUMENTS

| | | | |
|---|---|---|---|
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |

| | | | |
|---|---|---|---|
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,161,971 B2 | 4/2012 | Jaffe et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |

(56) References Cited

U.S. PATENT DOCUMENTS

| | | | |
|---|---|---|---|
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,600,467 | B2 | 12/2013 | Al-Ali et al. |
| 8,606,342 | B2 | 12/2013 | Diab |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,965,471 | B2 | 2/2015 | Lamego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,259,542 | B2 | 2/2016 | Acker et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |

(56) References Cited

U.S. PATENT DOCUMENTS

| | | | |
|---|---|---|---|
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |

(56)　　　　　　References Cited

U.S. PATENT DOCUMENTS

| RE47,353 | E | 4/2019 | Kiani et al. |
|---|---|---|---|
| 10,251,585 | B2 | 4/2019 | Al-Ali et al. |
| 10,251,586 | B2 | 4/2019 | Lamego |
| 10,255,994 | B2 | 4/2019 | Sampath et al. |
| 10,258,265 | B1 | 4/2019 | Poeze et al. |
| 10,258,266 | B1 | 4/2019 | Poeze et al. |
| 10,271,748 | B2 | 4/2019 | Al-Ali |
| 10,278,626 | B2 | 5/2019 | Schurman et al. |
| 10,278,648 | B2 | 5/2019 | Al-Ali et al. |
| 10,279,247 | B2 | 5/2019 | Kiani |
| 10,292,628 | B1 | 5/2019 | Poeze et al. |
| 10,292,657 | B2 | 5/2019 | Abdul-Hafiz et al. |
| 10,292,664 | B2 | 5/2019 | Al-Ali |
| 10,299,708 | B1 | 5/2019 | Poeze et al. |
| 10,299,709 | B2 | 5/2019 | Perea et al. |
| 10,299,720 | B2 | 5/2019 | Brown et al. |
| 10,305,775 | B2 | 5/2019 | Lamego et al. |
| 10,307,111 | B2 | 6/2019 | Muhsin et al. |
| 10,325,681 | B2 | 6/2019 | Sampath et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,335,033 | B2 | 7/2019 | Al-Ali |
| 10,335,068 | B2 | 7/2019 | Poeze et al. |
| 10,335,072 | B2 | 7/2019 | Al-Ali et al. |
| 10,342,470 | B2 | 7/2019 | Al-Ali et al. |
| 10,342,487 | B2 | 7/2019 | Al-Ali et al. |
| 10,342,497 | B2 | 7/2019 | Al-Ali et al. |
| 10,349,895 | B2 | 7/2019 | Telfort et al. |
| 10,349,898 | B2 | 7/2019 | Al-Ali et al. |
| 10,354,504 | B2 | 7/2019 | Kiani et al. |
| 10,357,206 | B2 | 7/2019 | Weber et al. |
| 10,357,209 | B2 | 7/2019 | Al-Ali |
| 10,366,787 | B2 | 7/2019 | Sampath et al. |
| 10,368,787 | B2 | 8/2019 | Reichgott et al. |
| 10,376,190 | B1 | 8/2019 | Poeze et al. |
| 10,376,191 | B1 | 8/2019 | Poeze et al. |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| 10,398,320 | B2 | 9/2019 | Kiani et al. |
| 10,405,804 | B2 | 9/2019 | Al-Ali |
| 10,413,666 | B2 | 9/2019 | Al-Ali et al. |
| 10,420,493 | B2 | 9/2019 | Al-Ali et al. |
| D864,120 | S | 10/2019 | Forrest et al. |
| 10,433,776 | B2 | 10/2019 | Al-Ali |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,284 | B2 | 11/2019 | Al-Ali et al. |
| 10,463,340 | B2 | 11/2019 | Telfort et al. |
| 10,470,695 | B2 | 11/2019 | Al-Ali et al. |
| 10,471,159 | B1 | 11/2019 | Lapotko et al. |
| 10,478,107 | B2 | 11/2019 | Kiani et al. |
| 10,503,379 | B2 | 12/2019 | Al-Ali et al. |
| 10,505,311 | B2 | 12/2019 | Al-Ali et al. |
| 10,512,436 | B2 | 12/2019 | Muhsin et al. |
| 10,524,706 | B2 | 1/2020 | Telfort et al. |
| 10,524,738 | B2 | 1/2020 | Olsen |
| 10,531,811 | B2 | 1/2020 | Al-Ali et al. |
| 10,531,819 | B2 | 1/2020 | Diab et al. |
| 10,531,835 | B2 | 1/2020 | Al-Ali et al. |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,548,561 | B2 | 2/2020 | Telfort et al. |
| 10,555,678 | B2 | 2/2020 | Dalvi et al. |
| 10,568,514 | B2 | 2/2020 | Wojtczuk et al. |
| 10,568,553 | B2 | 2/2020 | O'Neil et al. |
| RE47,882 | E | 3/2020 | Al-Ali |
| 10,575,779 | B2 | 3/2020 | Poeze et al. |
| 10,582,886 | B2 | 3/2020 | Poeze et al. |
| 10,588,518 | B2 | 3/2020 | Kiani |
| 10,588,553 | B2 | 3/2020 | Poeze et al. |
| 10,588,556 | B2 | 3/2020 | Kiani et al. |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |

(56) References Cited

U.S. PATENT DOCUMENTS

| | | | |
|---|---|---|---|
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali |
| D1,037,462 | S | 7/2024 | Al-Ali et al. |
| 12,029,844 | B2 | 7/2024 | Pauley et al. |
| 12,036,014 | B2 | 7/2024 | Eckerbom et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |
| 12,198,790 | B1 | 1/2025 | Al-Ali |
| 12,200,421 | B2 | 1/2025 | Campbell et al. |
| 12,207,901 | B1 | 1/2025 | Lapotko et al. |
| D1,060,680 | S | 2/2025 | Al-Ali et al. |
| D1,061,585 | S | 2/2025 | Indorf |
| D1,063,893 | S | 2/2025 | DeJong et al. |
| 12,220,207 | B2 | 2/2025 | Telfort et al. |
| 12,235,941 | B2 | 2/2025 | Kiani et al. |
| 12,236,767 | B2 | 2/2025 | Muhsin |
| D1,066,244 | S | 3/2025 | Lim et al. |
| D1,066,672 | S | 3/2025 | Al-Ali et al. |
| D1,068,656 | S | 4/2025 | Trevisan et al. |
| D1,071,195 | S | 4/2025 | Seung |
| D1,072,836 | S | 4/2025 | Indorf |
| D1,072,837 | S | 4/2025 | Ahmed et al. |
| 12,272,445 | B1 | 4/2025 | Kiani |
| D1,078,689 | S | 6/2025 | Hwang |
| D1,079,020 | S | 6/2025 | Hwang |
| 12,336,796 | B2 | 6/2025 | Al-Ali |
| D1,083,653 | S | 7/2025 | DeJong et al. |
| D1,085,102 | S | 7/2025 | Indorf et al. |
| 12,362,596 | B2 | 7/2025 | Barker et al. |
| 12,390,114 | B2 | 8/2025 | Novak, Jr. et al. |
| D1,092,244 | S | 9/2025 | DeJong et al. |
| D1,093,406 | S | 9/2025 | Indorf et al. |
| D1,094,735 | S | 9/2025 | DeJong et al. |
| D1,095,288 | S | 9/2025 | Lim |
| D1,095,483 | S | 9/2025 | DeJong et al. |
| 12,433,524 | B2 | 10/2025 | Al-Ali et al. |
| 12,440,128 | B2 | 10/2025 | Al-Ali et al. |
| D1,102,622 | S | 11/2025 | Al-Ali et al. |
| 12,478,272 | B2 | 11/2025 | Telfort et al. |
| 12,478,293 | B1 | 11/2025 | Al-Ali et al. |
| 12,495,967 | B2 | 12/2025 | Muhsin et al. |
| 2001/0034477 | A1 | 10/2001 | Mansfield et al. |
| 2001/0039483 | A1 | 11/2001 | Brand et al. |
| 2002/0010401 | A1 | 1/2002 | Bushmakin et al. |
| 2002/0055685 | A1 | 5/2002 | Levitsky et al. |
| 2002/0058864 | A1 | 5/2002 | Mansfield et al. |
| 2002/0133080 | A1 | 9/2002 | Apruzzese et al. |
| 2003/0013975 | A1 | 1/2003 | Kiani |
| 2003/0018243 | A1 | 1/2003 | Gerhardt et al. |
| 2003/0144582 | A1 | 7/2003 | Cohen et al. |
| 2003/0156288 | A1 | 8/2003 | Barnum et al. |
| 2003/0212312 | A1 | 11/2003 | Coffin, IV et al. |
| 2004/0045552 | A1 | 3/2004 | Curti et al. |
| 2004/0106163 | A1 | 6/2004 | Workman, Jr. et al. |
| 2004/0221846 | A1 | 11/2004 | Curti et al. |
| 2005/0055276 | A1 | 3/2005 | Kiani et al. |
| 2005/0103347 | A1 | 5/2005 | Curti et al. |
| 2005/0234317 | A1 | 10/2005 | Kiani |
| 2005/0279362 | A1 | 12/2005 | Colman et al. |
| 2006/0073719 | A1 | 4/2006 | Kiani |
| 2006/0161054 | A1 | 7/2006 | Reuss et al. |
| 2006/0189871 | A1 | 8/2006 | Al-Ali et al. |
| 2007/0068535 | A1 | 3/2007 | Colman et al. |
| 2007/0073116 | A1 | 3/2007 | Kiani et al. |
| 2007/0113847 | A1 | 5/2007 | Acker et al. |
| 2007/0180140 | A1 | 8/2007 | Welch et al. |
| 2007/0244377 | A1 | 10/2007 | Cozad et al. |
| 2007/0272247 | A1 | 11/2007 | Porat |
| 2007/0282478 | A1 | 12/2007 | Al-Ali et al. |
| 2008/0064965 | A1 | 3/2008 | Jay et al. |
| 2008/0094228 | A1 | 4/2008 | Welch et al. |
| 2008/0103375 | A1 | 5/2008 | Kiani |
| 2008/0216841 | A1 | 9/2008 | Grimes |
| 2008/0221418 | A1 | 9/2008 | Al-Ali et al. |
| 2008/0262369 | A1 | 10/2008 | Colman et al. |
| 2009/0036759 | A1 | 2/2009 | Ault et al. |
| 2009/0088656 | A1 | 4/2009 | Levitsky et al. |
| 2009/0093687 | A1 | 4/2009 | Telfort et al. |
| 2009/0095926 | A1 | 4/2009 | MacNeish, III |
| 2009/0137920 | A1 | 5/2009 | Colman et al. |
| 2009/0247984 | A1 | 10/2009 | Lamego et al. |
| 2009/0275813 | A1 | 11/2009 | Davis |
| 2009/0275844 | A1 | 11/2009 | Al-Ali |
| 2009/0275851 | A1 | 11/2009 | Colman et al. |
| 2009/0312662 | A1 | 12/2009 | Colman et al. |
| 2010/0004518 | A1 | 1/2010 | Vo et al. |
| 2010/0030040 | A1 | 2/2010 | Poeze et al. |
| 2010/0099964 | A1 | 4/2010 | O'Reilly et al. |
| 2010/0113955 | A1 | 5/2010 | Colman et al. |
| 2010/0139664 | A1 | 6/2010 | Curti et al. |
| 2010/0204603 | A1 | 8/2010 | Colman et al. |
| 2010/0234718 | A1 | 9/2010 | Sampath et al. |

(56) References Cited

U.S. PATENT DOCUMENTS

| | | |
|---|---|---|
| 2010/0262033 A1 | 10/2010 | Colman et al. |
| 2010/0270257 A1 | 10/2010 | Wachman et al. |
| 2010/0298734 A1 | 11/2010 | Colman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0066061 A1 | 3/2011 | Colman et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2011/0315757 A1 | 12/2011 | Colman et al. |
| 2012/0123231 A1 | 5/2012 | O'Reilly |
| 2012/0125332 A1 | 5/2012 | Niland et al. |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0005565 A1 | 1/2014 | Derrick |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |

(56) References Cited

U.S. PATENT DOCUMENTS

| | | |
|---|---|---|
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0350506 A1 | 11/2019 | Al-Ali et al. |
| 2019/0357812 A1 | 11/2019 | Poeze et al. |
| 2019/0357813 A1 | 11/2019 | Poeze et al. |
| 2019/0357823 A1 | 11/2019 | Reichgott et al. |
| 2019/0357824 A1 | 11/2019 | Al-Ali et al. |
| 2019/0358524 A1 | 11/2019 | Kiani |
| 2019/0365294 A1 | 12/2019 | Poeze et al. |
| 2019/0365295 A1 | 12/2019 | Poeze et al. |
| 2019/0374135 A1 | 12/2019 | Poeze et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2019/0388039 A1 | 12/2019 | Al-Ali |
| 2020/0000338 A1 | 1/2020 | Lamego et al. |
| 2020/0000340 A1 | 1/2020 | Wojtczuk et al. |
| 2020/0000415 A1 | 1/2020 | Barker et al. |
| 2020/0015716 A1 | 1/2020 | Poeze et al. |
| 2020/0021930 A1 | 1/2020 | Iswanto et al. |
| 2020/0029867 A1 | 1/2020 | Poeze et al. |
| 2020/0037453 A1 | 1/2020 | Triman et al. |
| 2020/0037891 A1 | 2/2020 | Kiani et al. |
| 2020/0037966 A1 | 2/2020 | Al-Ali |
| 2020/0046257 A1 | 2/2020 | Eckerbom et al. |
| 2020/0054253 A1 | 2/2020 | Al-Ali et al. |
| 2020/0060591 A1 | 2/2020 | Diab et al. |
| 2020/0060628 A1 | 2/2020 | Al-Ali et al. |
| 2020/0060629 A1 | 2/2020 | Muhsin et al. |
| 2020/0060869 A1 | 2/2020 | Telfort et al. |
| 2020/0074819 A1 | 3/2020 | Muhsin et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |

(56) References Cited

U.S. PATENT DOCUMENTS

| | | |
|---|---|---|
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |
| 2025/0037836 A1 | 1/2025 | Kiani |
| 2025/0100482 A1 | 3/2025 | Al-Ali et al. |
| 2025/0118415 A1 | 4/2025 | Olsen |
| 2025/0255764 A1 | 8/2025 | Stead |
| 2025/0278512 A1 | 9/2025 | Koo et al. |
| 2025/0281059 A1 | 9/2025 | Avendano |
| 2025/0288250 A1 | 9/2025 | Al-Ali et al. |
| 2025/0295366 A1 | 9/2025 | Al-Ali et al. |
| 2025/0302426 A1 | 10/2025 | Ha et al. |
| 2025/0311949 A1 | 10/2025 | Al-Ali et al. |

FOREIGN PATENT DOCUMENTS

| | | |
|---|---|---|
| IL | 145821 | 8/2011 |
| JP | 2003-038647 | 2/2003 |
| JP | 3108599 | 2/2005 |
| JP | 2007-512922 | 5/2007 |
| JP | 3157855 | 2/2010 |
| WO | WO 92/012751 | 8/1992 |
| WO | WO 03/068301 | 8/2003 |
| WO | WO 2005/055809 | 6/2005 |
| WO | WO 2012/006415 | 1/2012 |
| WO | WO 2015/121815 | 8/2015 |
| WO | WO 2016/118922 | 7/2016 |

OTHER PUBLICATIONS

US 2024/0016391 A1, 01/2024, Lapotko et al. (withdrawn)
Invitation to Pay Additional Fees received in PCT Appication No. PCT/US2016/014621, dated Apr. 18, 2016.
International Search Report and Written Opinion received in PCT Application No. PCT/US2016/014621, dated Jun. 30, 2016.
International Preliminary Report on Patentability and Written Opinion received in PCT Application No. PCT/US2016/014621, dated Aug. 3, 2017.

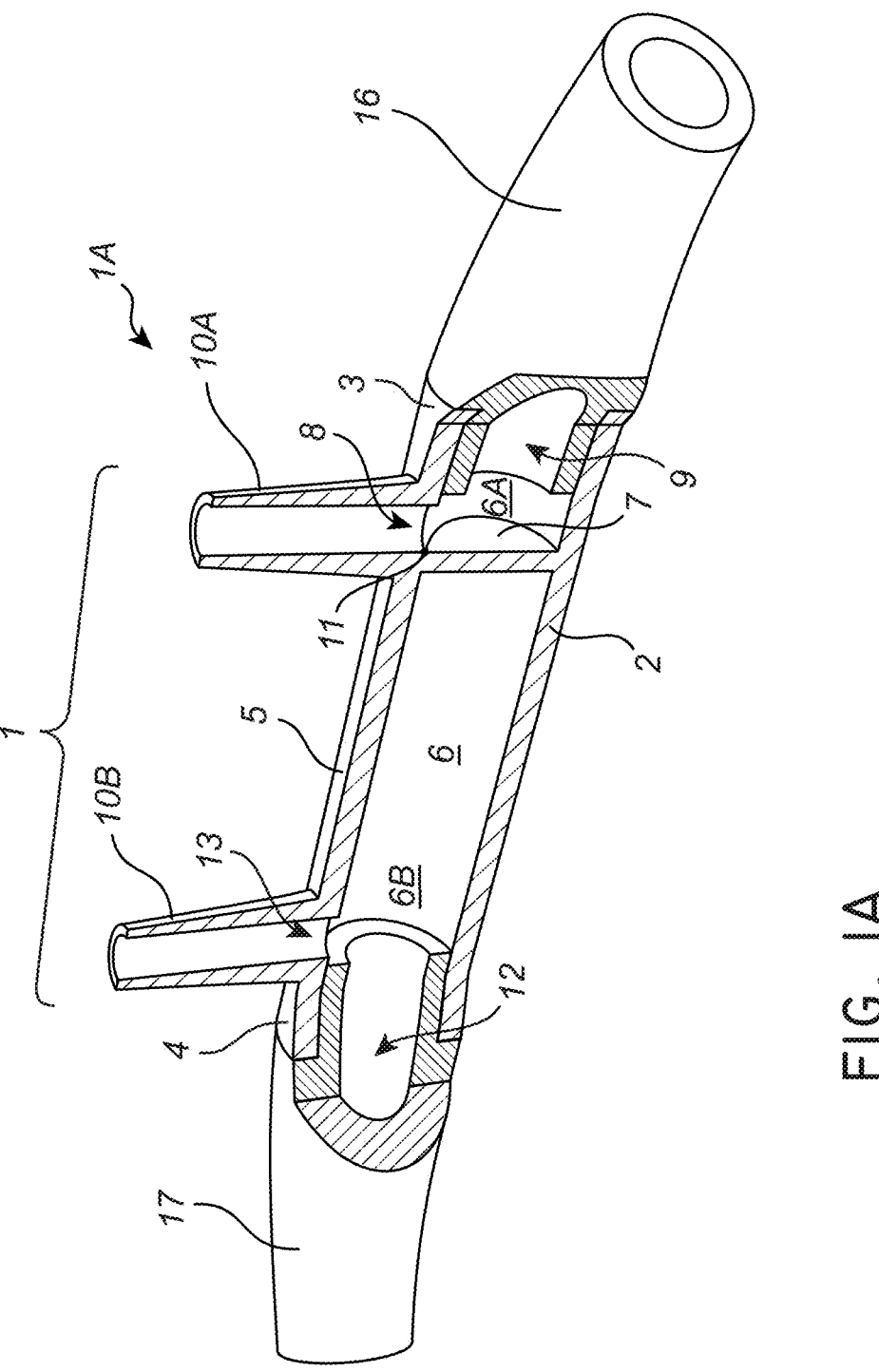
FIG. IA

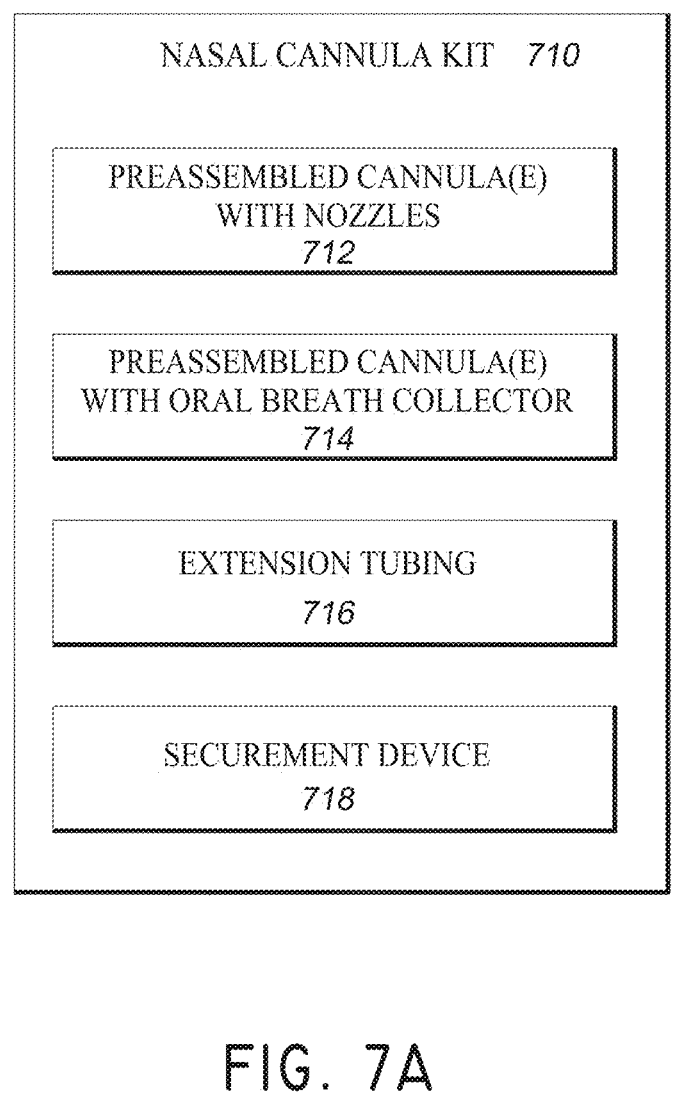

NASAL CANNULA KIT    *710*

PREASSEMBLED CANNULA(E)
WITH NOZZLES
*712*

PREASSEMBLED CANNULA(E)
WITH ORAL BREATH COLLECTOR
*714*

EXTENSION TUBING
*716*

SECUREMENT DEVICE
*718*

FIG. 7A

GAS SAMPLING KIT    *700*

| NASAL CANNULA KIT(S)  *710* | GAS SAMPLING LINE(S)  *720* | CAPNOGRAPH  *730* |

FIG. 7B

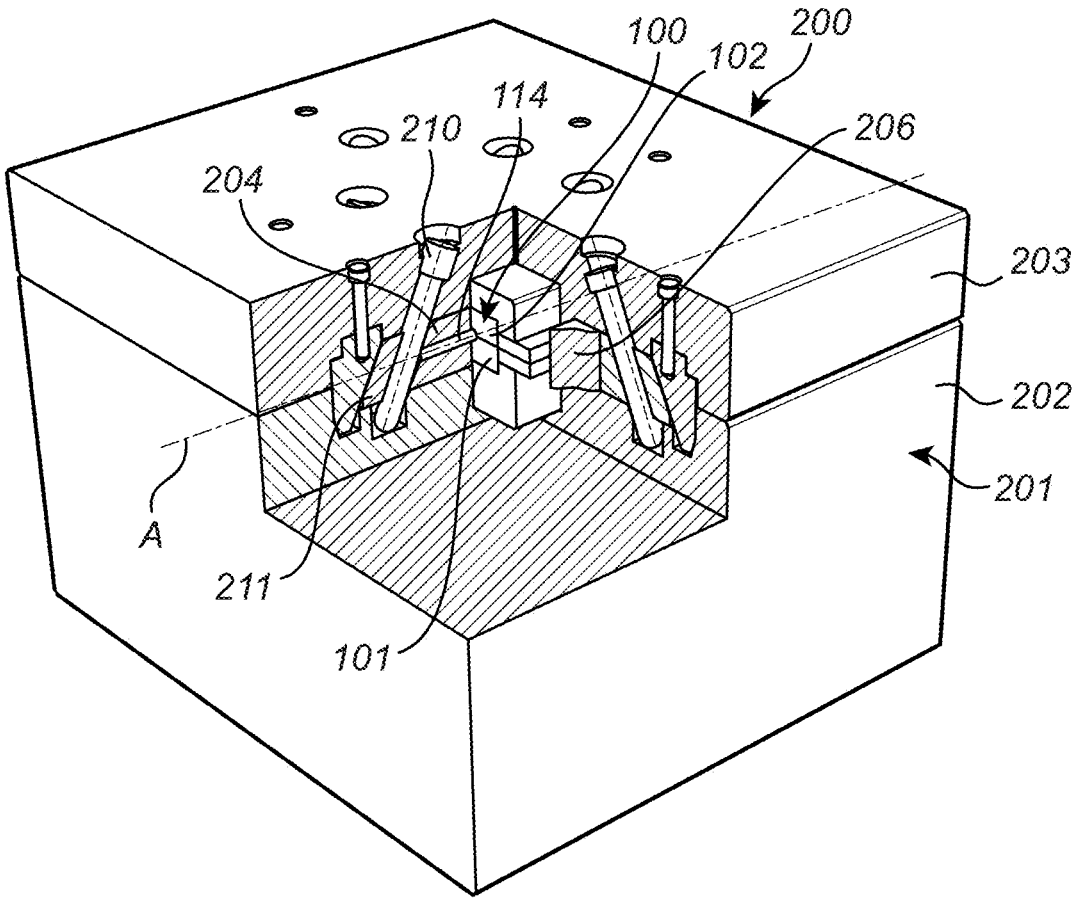
FIG. IIA

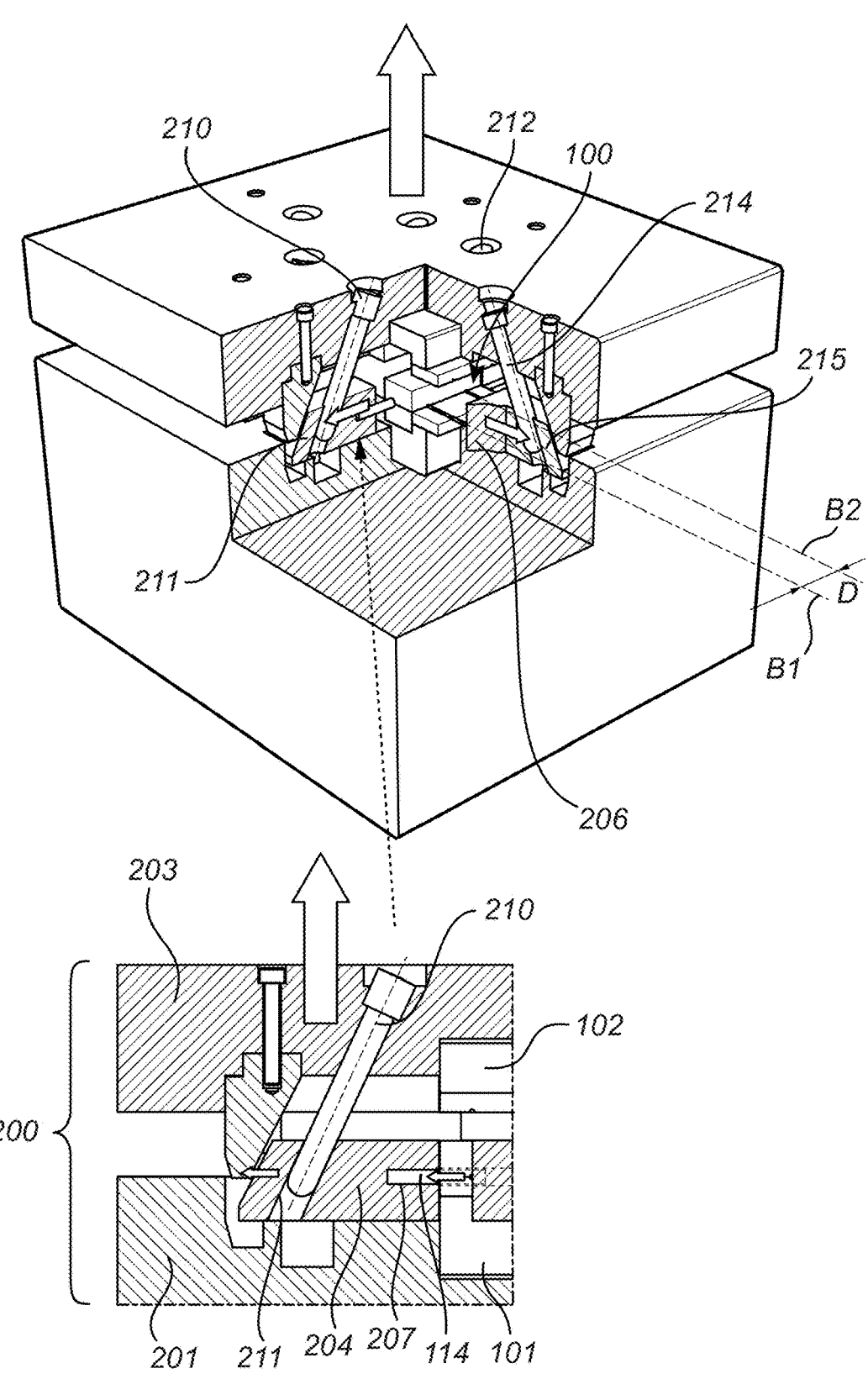
FIG. IIB

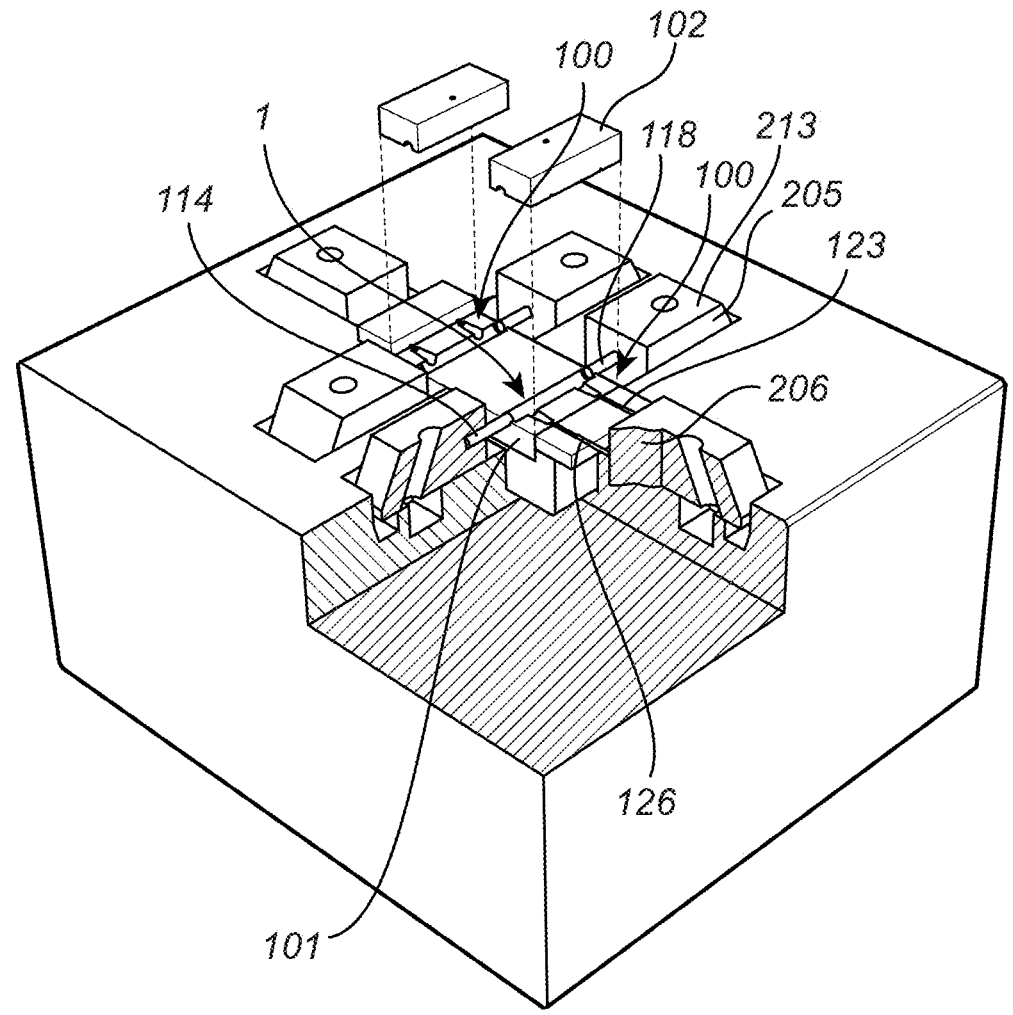
FIG. IIC

NASAL/ORAL CANNULA SYSTEM AND MANUFACTURING

CROSS-REFERENCE TO RELATED APPLICATIONS

The present application is a continuation of U.S. patent application Ser. No. 16/601,326 filed Oct. 14, 2019, which is a continuation of U.S. patent application Ser. No. 15/004, 695 filed Jan. 22, 2016, now U.S. Pat. No. 10,441,196, which claims the benefit under 35 U.S.C. § 119(e) of U.S. Provisional Patent Application No. 62/107,232, filed on Jan. 23, 2015, entitled "NASAL/ORAL CANNULA SYSTEM AND MANUFACTURING," the contents of which is hereby incorporated by reference herein in its entirety and for all purposes.

TECHNICAL FIELD

The present disclosure relates to a nasal/oral cannula for the collection of a flow of exhaled gases.

BACKGROUND

In health care, it is often desirable to analyze and monitor the gas composition of a patient's exhaled and/or inhaled breathing gases. For instance, measurement of respiratory $CO_2$, $O_2$, $N_2O$, and anesthetic agents, such as halothane, isoflurane, enflurane, sevoflurane or desflurane, may be useful in the care of critically ill patients undergoing anesthesia. In some emergency care situations involving manual ventilation, it may typically be sufficient to monitor a patient's breathing with a simple $CO_2$ analysis.

Capnography is the monitoring of the concentration or partial pressure of carbon dioxide ($CO_2$) in respiratory gases, and provides real-time information regarding $CO_2$ exhalation and respiratory rates as well as a rapid and reliable assessment of a patient's ventilatory, circulatory and metabolic function. Although the terms capnography and capnometry are sometimes considered synonymous, capnometry suggests measurement without a continuous written record or waveform. Typically in capnography and capnometry, a gas analyzing device is placed in the respiratory circuit of a patient to sample exhaled and/or inhaled breathing gases and calculate gas concentrations directly in the respiratory circuit.

Measurement of end tidal $CO_2$ can also provide useful information regarding $CO_2$ production, pulmonary (lung) perfusion, alveolar ventilation, respiratory patterns, and elimination of $CO_2$ from an anesthesia breathing circuit or ventilator. The gas sample measured at the end of a person's exhalation is called the "end-tidal" gas sample. The amount of $CO_2$ in a person's end-tidal breath can indicate the overall efficiency of the cardio-pulmonary system and quality of breathing. For example, an overly high concentration of $CO_2$ can indicate shallow breathing and poor oxygen intake. Thus, capnographs are used in hospitals and other medical institutions for monitoring the condition of a patient's respiratory system, pulmonary perfusion, and metabolism, and are often used for patients in intensive care or under anesthesia. Gas analyzers, including capnographs, can also be used in a wide range of other circumstances, for example ventilator management and weaning, metabolic measurements and nutritional assessment, and automated drug infusion safety.

The accuracy of the analysis of exhaled gases depends on the ability of a sampling system to move a gas sample from the patient to the gas analyzer while maintaining a smooth, laminar flow of gases, such that there are as few as possible alterations to the waveform representing the measured concentration of the gases. An accurate waveform depicting the concentration of the gas is critical for accurate patient monitoring and diagnosis.

Different types of oral/nasal cannulae are used to collect exhaled gas samples from patients in order to monitor respiration and other patient parameters. Some cannulae additionally deliver oxygen and/or other therapeutic gases, for example anesthetic gases, to the patient as needed.

SUMMARY

Cannulae such as those described above work well for the delivery of oxygen to a patient, since the flow of delivered oxygen is relatively high. However, when considering the collection of exhaled gases from the patient, the gas flow is considerably lower. Accordingly, these cannulae may produce a pronounced problem in the analysis of exhaled gases due to the presence of the space in the tube between the partition and the prong through which the exhaled gas enters. Such space is referred to herein as a "void volume" because it does not form part of the pathway for the flow of gases and hence is unproductive. The presence of such a void volume is a significant hindrance to the accurate analysis of exhaled gases because it creates turbulence and backflow within the cannula. Thus, such nasal cannulae may decrease the accuracy and efficiency of analysis of collected exhaled gases.

Further, available production methods for nasal/oral cannula systems are generally associated with limitations, for example related to suitable starting materials and manufacturing processes. Injection molding generally requires stiff and hard material, which makes it difficult to make complicated details, and also leads to uncomfortable end products. Dip molding allows the use of soft, more user-friendly materials, but similarly suffers from the disadvantage of imprecise production. Another problem with the existing production methods stems from the need for a vast number of different molds in order to produce cannula systems of different shapes and sizes. Also, the conventional use of glue in the assembly of modular systems leads to thick boundary layers between pieces, which may in turn have a disturbing effect on gas flowing through the system.

Accordingly, there is a need for a nasal/oral cannula which is easy to manufacture and which provides for accurate analysis of exhaled gases, possibly in combination with the supply of a treating gas, such as oxygen. In addition, there is a need for an improved method for manufacturing nasal/oral cannula systems, which allows for the use of comfortable and soft materials, as well as for a simple and flexible way of producing reliable cannula systems of different shapes and sizes.

The above-described problems with existing cannulae, among others, are resolved or reduced by some embodiments of the modular nasal cannula systems described herein. Similarly, the above-described manufacturing problems, among others, are resolved or reduced in some embodiments of the cannula manufacturing systems and techniques described herein.

In some aspects of the disclosure, a nasal/oral cannula for collecting a flow of exhaled gases comprising an elongated tubular body having a first and a second end portion, a surface and an internal volume; a wall internally disposed within said tubular body, said wall defining a first subvolume of said internal volume in the lengthwise direction of the tubular body; and an inlet extending through said surface, for introducing exhaled gases into said first subvolume is disclosed. In some embodiments, said first end portion defines an exit port for exhaled gases from said subvolume, and said wall is advantageously arranged adjacent to said inlet.

The arrangement of the wall adjacent to the inlet provides for a very advantageous cannula construction, since it minimizes the risk for disturbances in the gas flow. In particular, this arrangement of the wall minimizes or eliminates the void volume in the tubular body, which in turn provides for a smooth, laminar flow of gases in the cannula system and, as a consequence, reliable analysis results. In some embodiments, said wall is arranged to provide a flow path for exhaled gases from said inlet to said exit port, such that essentially the entire first subvolume forms part of said flow path.

In some embodiments, said tubular body may further comprise a length L, and said inlet may be arranged at a distance of less than L/2 from said first end portion. In other embodiments, said tubular body may comprise a length L, and said inlet may be arranged at a distance of about L/2 from said first end portion. In some embodiments, the nasal/oral cannula may further comprise a first additional inlets through said surface.

In some embodiments of the nasal/oral cannula, said internally disposed wall within said tubular body also defines a second subvolume of said internal volume in the lengthwise direction of the tubular body, and said second end portion defines an entrance port for allowing a treating gas into the second subvolume. In some embodiments the nasal/oral cannula may further comprise an outlet through said surface, for transferring a treating gas from said second subvolume to the respiratory system of a patient.

In some embodiments, a nasal/oral cannula system may comprise a nasal/oral cannula as described above and/or below, a first nozzle adapted for the transport of exhaled gases from the cannula, and a sampling tube adapted for the transport of exhaled gases from the cannula to an analyzer. In some embodiments, a nasal/oral cannula system may further comprise a second nozzle adapted for the supplementation of a treating gas to the cannula, and a treating gas tube adapted for the transport of a treating gas from a treating gas source to the cannula.

In some aspects of the disclosure, a method for the manufacture of a nasal/oral cannula system comprising the steps of: (1) providing, by injection molding of a manufacturing material, a cannula comprising an elongated tubular body having a first and a second end portion, a surface, and an inlet extending through said surface, said elongated tubular body comprising a wall internally disposed within said tubular body; (2) providing, by injection molding of a manufacturing material, a first nozzle, and (3) assembling said nasal/oral cannula system by solvent bonding, is disclosed.

In some embodiments of the method, said cannula is provided by providing a cannula mold shaped to create a desired outer shape of said cannula; providing a cannula cavity, including a wall cavity, within the cannula mold with the aid of a first and second insert and a first pin, said cannula cavity, including said wall cavity, corresponding to the shape of said cannula; and filling the cannula cavity, including said wall cavity, with said manufacturing material.

In some embodiments of the method, said wall cavity is placed in a desired position within said cannula mold by movement of the first and second inserts. This embodiment therefore provides for a simple and flexible way of disposing the wall in a suitable position within the tubular body of the cannula. In particular, this method provides for easy arrangement of the wall in practically all positions within the tubular body by a simple movement of the first and second cavity tools.

In some embodiments, the nasal/oral cannula system may further comprise an oral breath collector, and the method may further comprise the step of providing, by injection molding, an oral breath collector.

In some embodiments, said first nozzle is provided by providing a nozzle mold shaped to create a desired outer shape of said first nozzle; providing a nozzle cavity within the nozzle mold with the aid of two cavity tools, said nozzle cavity corresponding to the shape of said nozzle; and filling the nozzle cavity with said manufacturing material.

In some aspects of the disclosure, a manufacturing tool configured for use with a mold as described herein is disclosed. In some embodiments, the tool comprises a tool body, a mold as described above supported by the tool body, a first device supporting a first insert and arranged to move the first insert between a molding position and the retracted position, a second device supporting a second insert and arranged to move the second insert between the molding position and the retracted position, a third device supporting an insert pin and arranged to move the insert pin between the molding position and the retracted position, wherein the first and second devices are configured to introduce the first and second inserts to the desired position to form the wall in the cannula.

In some embodiments of the tool, the first and second inserts are lockable within respective first and second devices at a plurality of longitudinal positions so as to allow for adjustment of the position of the wall within the manufactured cannula.

In some embodiments of the tool, the third device is configured to support at least two insert pins in a plurality of different position within the third device so as to allow the tool to adapt for molds intended for cannulae of different sizes.

In some embodiments, the tool comprises a first portion and a second portion and is further configured such that the movement of the first portion relative to the second portion mechanically causes the first, second, and third devices to move between a molding position and a release position.

In some embodiments, the tool and the mold are configured to be adjustable in order to mold cannulas of different sizes and configurations. For example, in some embodiments, the mold includes adjustable inserts that can be positioned at different locations that correspond to different placements of a wall within the cannula. In some embodiments, the inserts are adjustable by adjusting their placement within first and second devices of the tool. In some embodiments, the mold includes adjustable pin inserts configured to vary the distance between hollow prongs of the cannula in order to adjust the size for adults, children, and infants. In some embodiments, the pin inserts are adjustable by changing their position within the third device of the tool.

Other aspects of the disclosure relate to a nasal/oral cannula system obtainable by any of the methods described above and/or below and to all possible combinations of the features recited above.

BRIEF DESCRIPTION OF THE DRAWINGS

Throughout the drawings, reference numbers can be reused to indicate correspondence between referenced elements. The drawings are provided to illustrate embodiments of the present disclosure and do not to limit the scope thereof.

FIG. 1A shows a cutaway view an embodiment of a cannula that can be used to collect exhaled gases from one of a patient's nostrils while also supplying a treating gas to the patient's other nostril.

FIG. 7A illustrates a block diagram of one embodiment of a nasal cannula kit.

FIG. 7B illustrates a block diagram of one embodiment of a gas sampling kit.

FIG. 11A shows a cutaway view of a tool configured for use with a mold, such as the mold depicted in FIGS. 9A and 9B, with the tool arranged in a closed or molding position.

FIG. 11B shows a cutaway view of the embodiment of the tool of FIG. 11A as the tool is transitioning from the closed, molding position to an open position.

FIG. 11C shows a cutaway view of the embodiment of to the tool of FIGS. 11A and 11B in an open position.

DETAILED DESCRIPTION

Figure 1B:
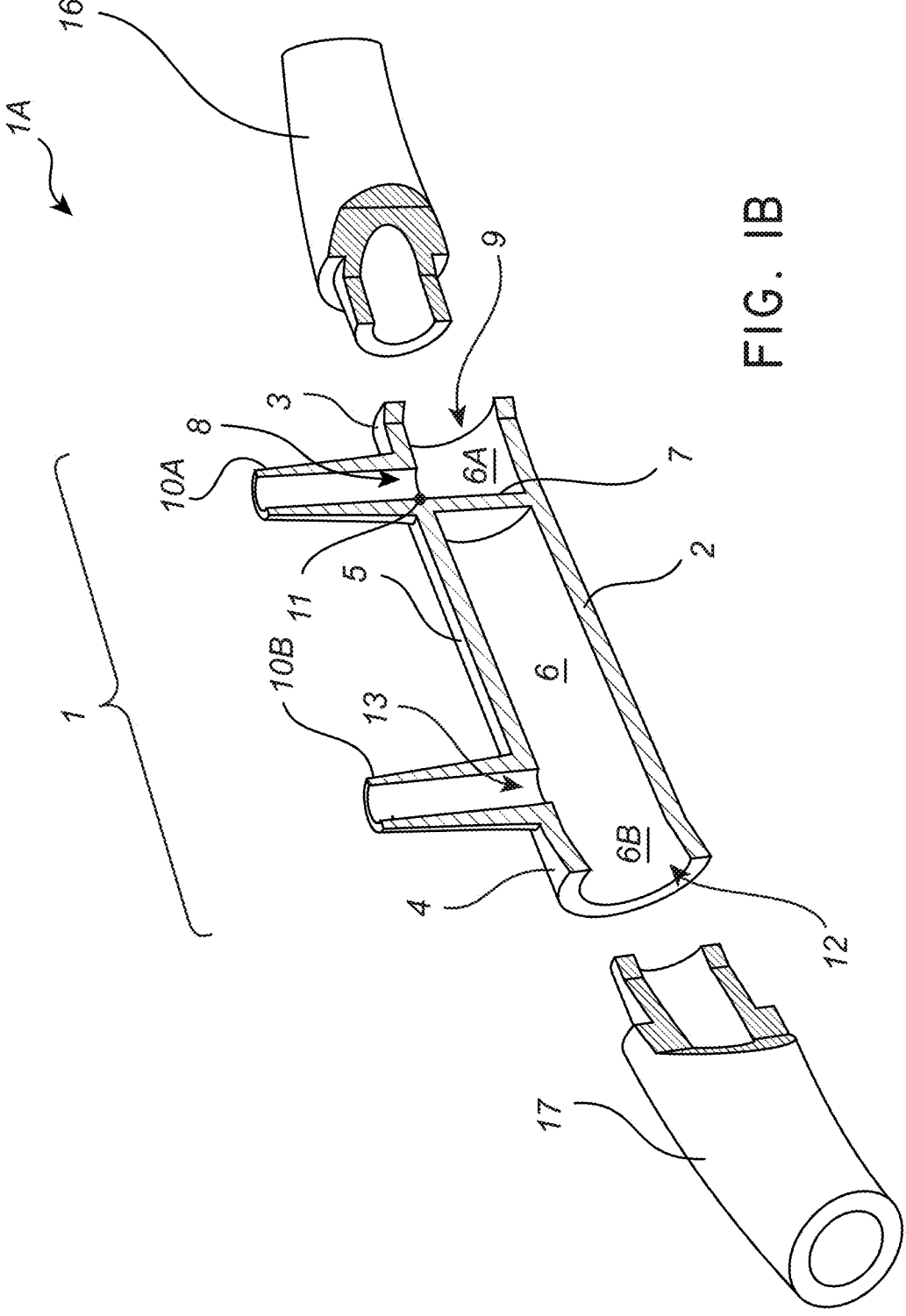
FIG. 1B shows an exploded view of the embodiment of FIG. 1A producible with the methods as described herein.

Nasal/oral or respiratory cannulae as described herein can provide for improved analysis of exhaled gases, for example $CO_2$, from a patient. In particular, the structure of the nasal/oral cannulae can beneficially overcome the problem of "void volumes" that can lead to inaccurate analysis results.

One noteworthy aspect of the present disclosure is the particular placement of a gas-tight inner wall within the cannula in order to define inhalation and exhalation compartments. In the research work leading to the development of the embodiments of cannulae described herein, it was found that the placement of such a wall placed in close proximity to, adjacent to and/or adjoining the inlet for exhaled gases, provides for a substantially undisturbed gas flow and, as a consequence, reliable and accurate analysis results, as will be described more fully below.

By placing the wall in immediate or near immediate connection with the inlet, the void volume can be minimized or eliminated, which provides for a smooth, laminar flow of gases from the patient to a gas analyzer. When there are several inlets for exhaled gases, the wall can be placed in connection to the inlet which is located at the farthest distance from the point where the gases exit the cannula.

As will be described in greater detail below, cannulae, following the principles herein disclosed, can take the form of at least three principal different embodiments, among others:

Embodiment 1: Exhaled gases are collected from one of a patient's nostrils. The collection of exhaled gases from one nostril may be combined with the supplementation of a treating gas to the patient's other nostril.

Embodiment 2: Exhaled gases are collected from the mouth of a patient. The collection of exhaled gases from the mouth of a patient may be combined with the collection of exhaled gases from one or both nostrils of a patient, and optionally also with supplementation of a treating gas to the other nostril.

Embodiment 3: Exhaled gases are collected from both nostrils of a patient. The collection of exhaled gases from both nostrils of a patient may be combined with the collection of exhaled gases from the mouth of a patient.

These three non-limiting principal cannulae embodiments, as well as combinations thereof, will be described in further detail below with reference to the attached drawings. In the following description, specific details are given to provide a thorough understanding of the examples. However, in some embodiments, the examples may be practiced without these specific details.

FIG. 1A depicts an embodiment of a cannula configured to collect gas from one of a patient's nostrils while also providing a treating gas to the patient's other nostril. It should be noted, however, that the concurrent supplementation of a treating gas is an optional feature of this embodiment.

The cannula system 1A comprises a cannula 1 and first and second nozzles 16, 17. The cannula 1 comprises an elongated tubular body 2 for the collection of gases exhaled through a first nostril (not shown) of a patient. The tubular body 2 has a first end portion 3 and a second end portion 4. The first end portion 3 may further define an exit port 9 for exhaled gases. The exhaled gases enter the tubular body 2 via an inlet 8, which is configured as a hole extending through a surface 5 of the tubular body 2. The tubular body 2 is preferably essentially cylindrical and has a length L measured between first end portion 3 and second end portion 4. In this embodiment, the inlet 8 is preferably arranged at a distance of less than L/2 from said first end portion 3. The inlet 8 is thereby adapted to receive exhaled gases from the first nostril of the patient. Gases exhaled by the patient through the first nostril enter the cannula through the inlet 8 and exit the cannula system 1A through the exit port 9 and first nozzle 16.

A wall 7 is internally disposed within the tubular body 2 in order to divide an internal volume 6 of the tubular body 2 into a first subvolume 6A and a second subvolume 6B. The first subvolume 6A is arranged in the lengthwise direction toward the first end portion 3 of the tubular body 2. In some embodiments, the inlet 8 preferably comprises a first hollow prong 10, which allows for fluid communication into the subvolume 6A of the tubular body 2. The first hollow prong 10A may be configured to be inserted into the first nostril of the patient. The hollow prong 10A is preferably molded integrally with the tubular body 2; however, the hollow prong 10A may alternatively be sealingly adhered to the tubular body by other means, including use of an adhesive composition.

The wall 7 is arranged directly adjacent, or in close proximity, to the inlet 8. As used herein, "adjacent" and "directly adjacent" to the inlet is meant to signify that the wall 7 is arranged in immediate contact with the inlet 8 so that no void volume for the flow of exhaled gases is created between the wall 7 and the inlet 8, or that the wall 7 is arranged in near immediate contact with the inlet 8 so that void volume is acceptably low. This placement is described throughout, and especially in relation to FIG. 5, which will be discussed more fully below. Alternatively, the wall 7 can be located in close proximity to the inlet 8 in order to substantially reduce the void volume to acceptable limits.

When the inlet 8 comprises a hollow prong 10, the wall 7 can be seen to constitute an extension of an inner side of the hollow prong 10A from the tangential point 11 where the hollow prong 10A is joined with the inner side of the tubular body 2. The wall 7 thereby provides for an uninterrupted flow path for the exhaled gases from the inlet 8 to the exit port 9 where essentially the entire subvolume 6A forms part of the flow path. Thus, gases exhaled by the patient through the first nostril enter the cannula through the inlet 8 and exit the cannula through the exit port 9 without significant interruption, turbulence, or back flow.

The embodiment of the cannula depicted in FIG. 1A is also configured to provide for the supplementation of a treating gas to a second nostril (not shown) of the patient. In this embodiment, the wall 7 defines a second subvolume 6B in the internal volume 6 of the tubular body 2. The subvolume 6B is arranged in the lengthwise direction toward the second end portion 4 of the tubular body 2. The treating gas enters the second subvolume 6B through an entrance port 12, and exits the subvolume 6B through an outlet 13 formed as a hole extending through the surface 5. The treating gas is thereby transferred to the respiratory system of a patient. The outlet 13 preferably also comprises a hollow prong 10B configured to deliver the treating gas to the second nostril of the patient.

FIG. 1B illustrates an exploded view of the components of the embodiment of the cannula system 1A of FIG. 1A. As illustrated, the cannula 1 and nozzles 16, 17 can be separately manufactured, for example by injection molding. These separate components can then be assembled by solvent bonding. For example, an inserting end of nozzle 16 can be sized to fit within exit port 9. An exterior surface of the inserting end of nozzle 16 may be coated or provided with a solvent for solvent bonding and then inserted into exit port 9. Similarly, inserting end of nozzle 17 can be sized to fit within an entrance port 12. An exterior surface of the inserting end of nozzle 17 may be coated or provided with a solvent for solvent bonding and then inserted into entrance port 12. In alternative embodiments these components may be configured for a substantially fluid-tight press fit.

Figure 2A:
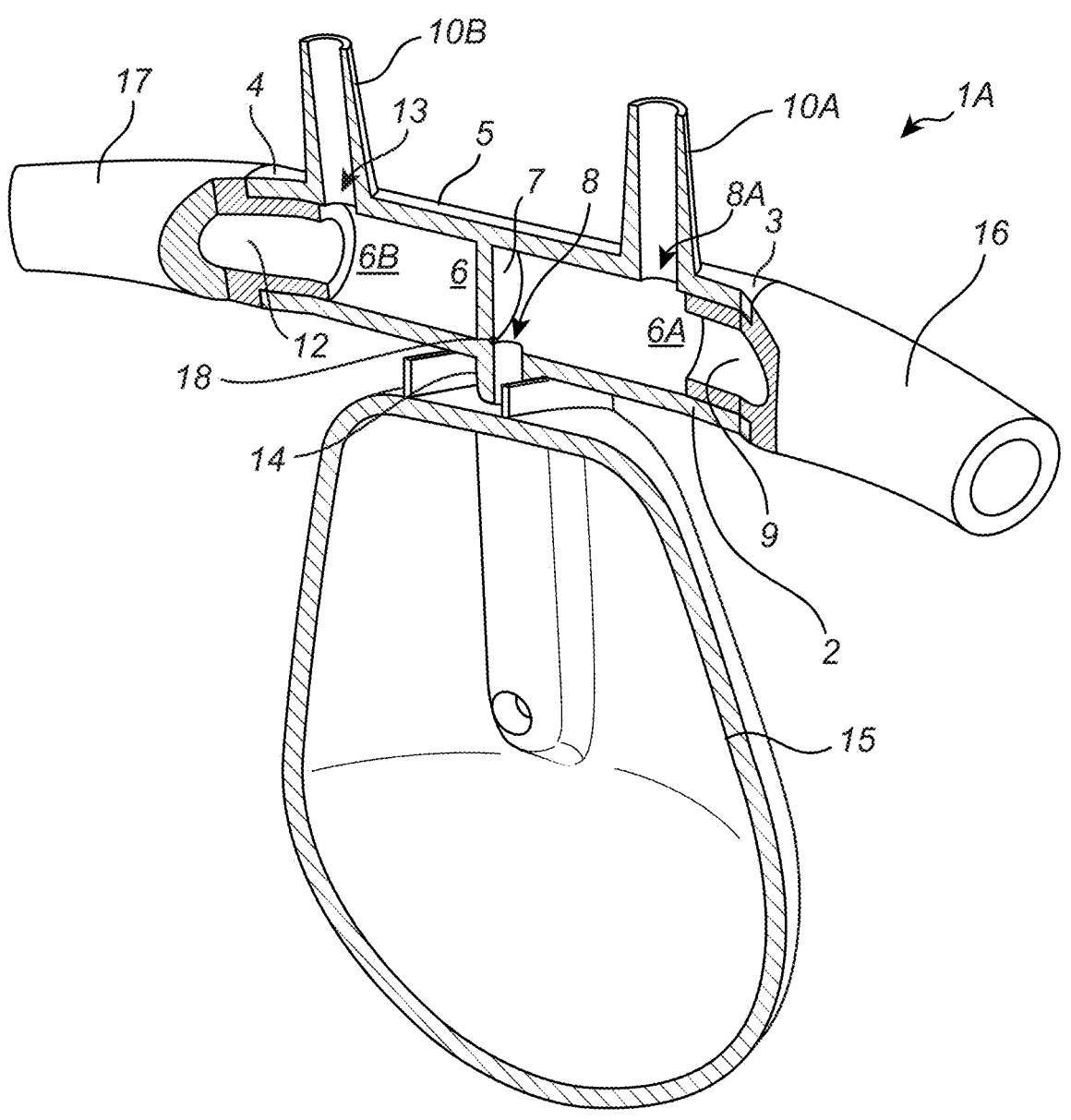
FIG. 2A shows a cutaway view of an additional embodiment of a cannula that is configured to collect exhaled gases from the mouth of a patient in addition to collecting exhaled gases from one of a patient's nostrils while also supplying a treating gas to the patient's other nostril.

FIG. 2A depicts an alternative embodiment of a cannula system 1A according to the present disclosure that is configured to collect gases exhaled from the mouth and first nostril of a patient. It should be noted, however, that the concurrent collection of exhaled gases from the first nostril is an optional feature of this embodiment. The embodiment of FIG. 2A can also optionally be configured to provide a supplemental treating gas to the second nostril of the patient. The cannula system 1A can comprise a cannula 1, first and second nozzles 16 and 17, and an oral breath collector 15.

The cannula 1 comprises an elongated tubular body 2 for the collection of gases exhaled trough the mouth and/or first nostril of a patient (not shown). The tubular body 2 has respective first and second end portions 3, 4. The first end portion 3 defines an exit port 9 for exhaled gases. The exhaled gases enter the tubular body 2 via an inlet 8 configured as a hole extending through a surface 5 of the tubular body 2. In some embodiments, the tubular body 2 is preferably essentially cylindrical and has a length L measured between the first and second end portions 3, 4, where the inlet 8 is preferably arranged at a distance of about L/2 from said first end portion 3, such as substantially between the first and the second end portions 3, 4. The inlet 8 is thereby adapted to receive exhaled gases from the mouth of a patient.

In addition, the cannula may comprise a first additional inlet 8A also configured as a hole extending through said surface 5. The first additional inlet 8A is preferably arranged at a distance of less than L/2 from said first end portion 3, such as in proximity to the first end portion 3. The first additional inlet 8A is disposed on the opposite side of the cannula 1 of the inlet 8; or, in other words, if the inlet is disposed on the bottom of the cannula 1, the first additional inlet 8A is disposed on the top. The first additional inlet 8A is thereby adapted to receive exhaled gases from the first nostril of a patient. The first additional inlet 8A preferably comprises a hollow prong 10A configured for insertion into the first nostril of the patient. Thus, gases exhaled by the patient through the mouth enter the cannula through the inlet 8 and gases exhaled by the patient through the first nostril enter the cannula through the first additional inlet 8A. The exhaled gases exit the cannula through the exit port 9 and first nozzle 16.

A wall 7 is internally disposed within the tubular body 2 in order to define a first subvolume 6A of the tubular body 2 into which exhaled gases are introduced. The subvolume is arranged in the lengthwise direction of the tubular body 2 toward the first end portion 3 of the tubular body 2. Preferably, the inlet 8 comprises a hollow prong 14, which allows for fluid communication into the first subvolume 6A of the tubular body 2. An oral breath collector 15, a so-called "scoop," may be connected to said hollow prong 14. The oral breath collector 15 is configured to cover the mouth of a patient using the cannula system 1A.

The wall 7 is arranged adjacent to the inlet 8. As above, "adjacent" to the inlet 8 signifies that the wall 7 is arranged in immediate, or near-immediate, contact with the opening 8 so that no, or acceptably low, void volume for the flow of exhaled gases is created between the wall 7 and the inlet 8. When the inlet 8 comprises a hollow prong 14, the wall 7 can be seen to constitute an extension of an inner side of the hollow prong 14 from the tangential point 18 where the hollow prong 14 is joined with the inner side of the tubular body 2.

The wall 7 thereby provides for a substantially uninterrupted flow path for the exhaled gases from the inlets 8, 8A to the exit port 9, and essentially the entire subvolume 6A forms part of the flow path. Thus, gases exhaled by the patient through the mouth and the first nostril enter the cannula through the inlets 8, 8A and exit the cannula through the exit port 9 without any substantial interruption, turbulence, or back flow.

In some embodiments, the cannula depicted in FIG. 2A, may also provide for the supplementation of a treating gas to a second nostril (not shown) of the patient. In this embodiment, the wall 7 defines a second subvolume 6B in the internal volume 6 of the tubular body 2. The subvolume 6B is arranged in the lengthwise direction toward the second end portion 4 of the tubular body 2. The treating gas enters the second subvolume 6B through an entrance port 12, and exits the subvolume 6B through an outlet 13 formed as a hole extending through the surface 5. The outlet 13 preferably comprises a hollow prong 10B configured for insertion into the patient's second nostril. The treating gas may thereby be transferred to the respiratory system of a patient.

Figure 2B:
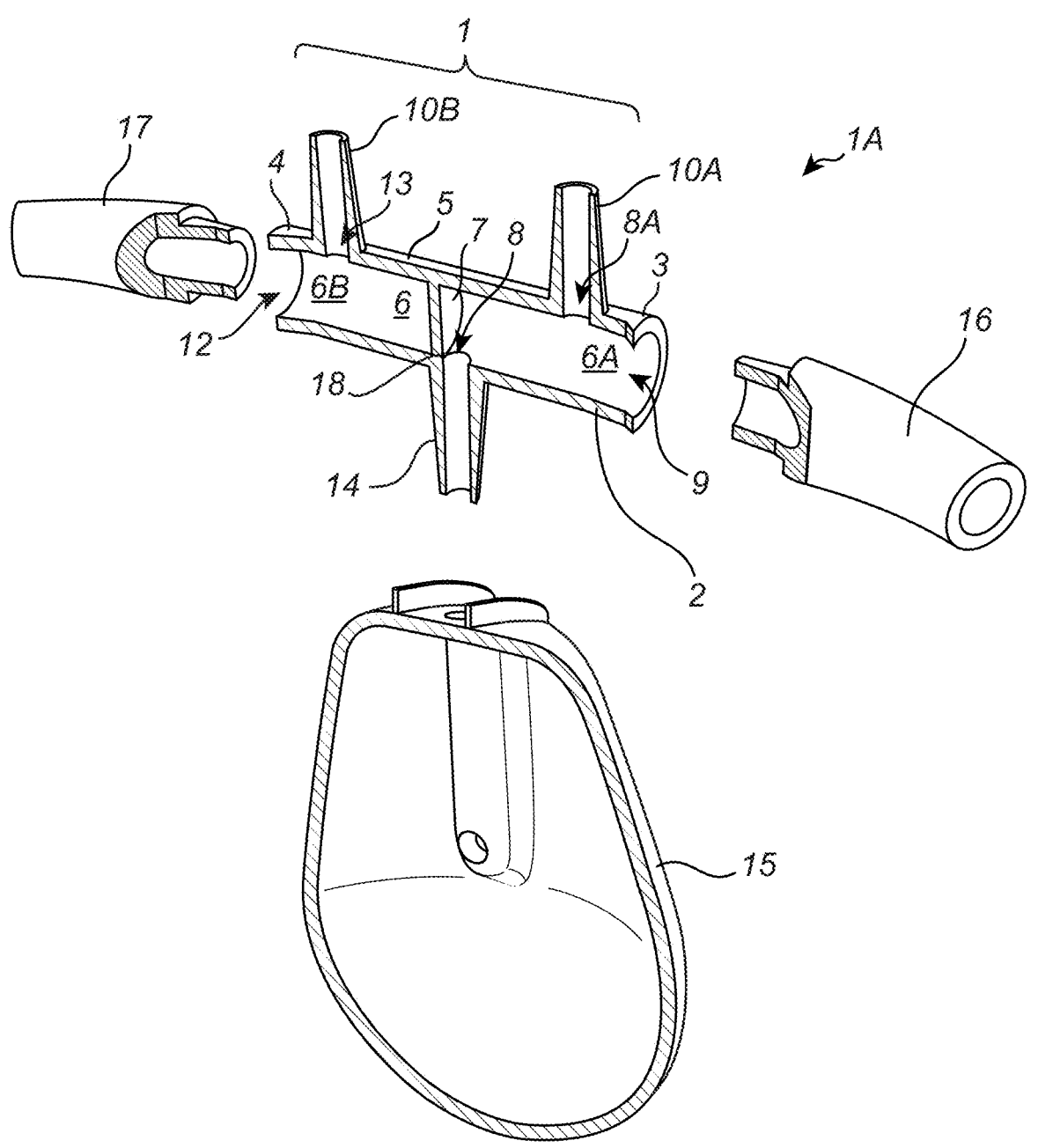
FIG. 2B shows an exploded view of the embodiment of FIG. 2A producible with the methods as described herein.

FIG. 2B illustrates an exploded view of the components of the cannula system 1A of embodiment shown in FIG. 2A. As illustrated, the cannula 1 and nozzles 16, 17 can be separately manufactured, for example by injection molding. These separate components can be assembled by solvent bonding. For example, an inserting end of nozzle 16 can be sized to fit within exit port 9. An exterior surface of the inserting end of nozzle 16 may be coated or provided with a solvent for solvent bonding and then inserted into exit port 9. Similarly, inserting end of nozzle 17 can be sized to fit within an entrance port 12. An exterior surface of the inserting end of nozzle 17 may be coated or provided with a solvent for solvent bonding and then inserted into entrance port 12. An aperture in the top of the oral breath collector 15 can be sized to receive hollow prong 14, and the breath collector may include a portion on the interior of the breath collector that extends around hollow prong 14 once inserted. An exterior surface of the prong 14 can be coated or provided with solvent for solvent bonding and then inserted into the aperture of the oral breath collector 15. In alternative embodiments, these components may be configured for a substantially fluid-tight press fit.

Figure 3A:
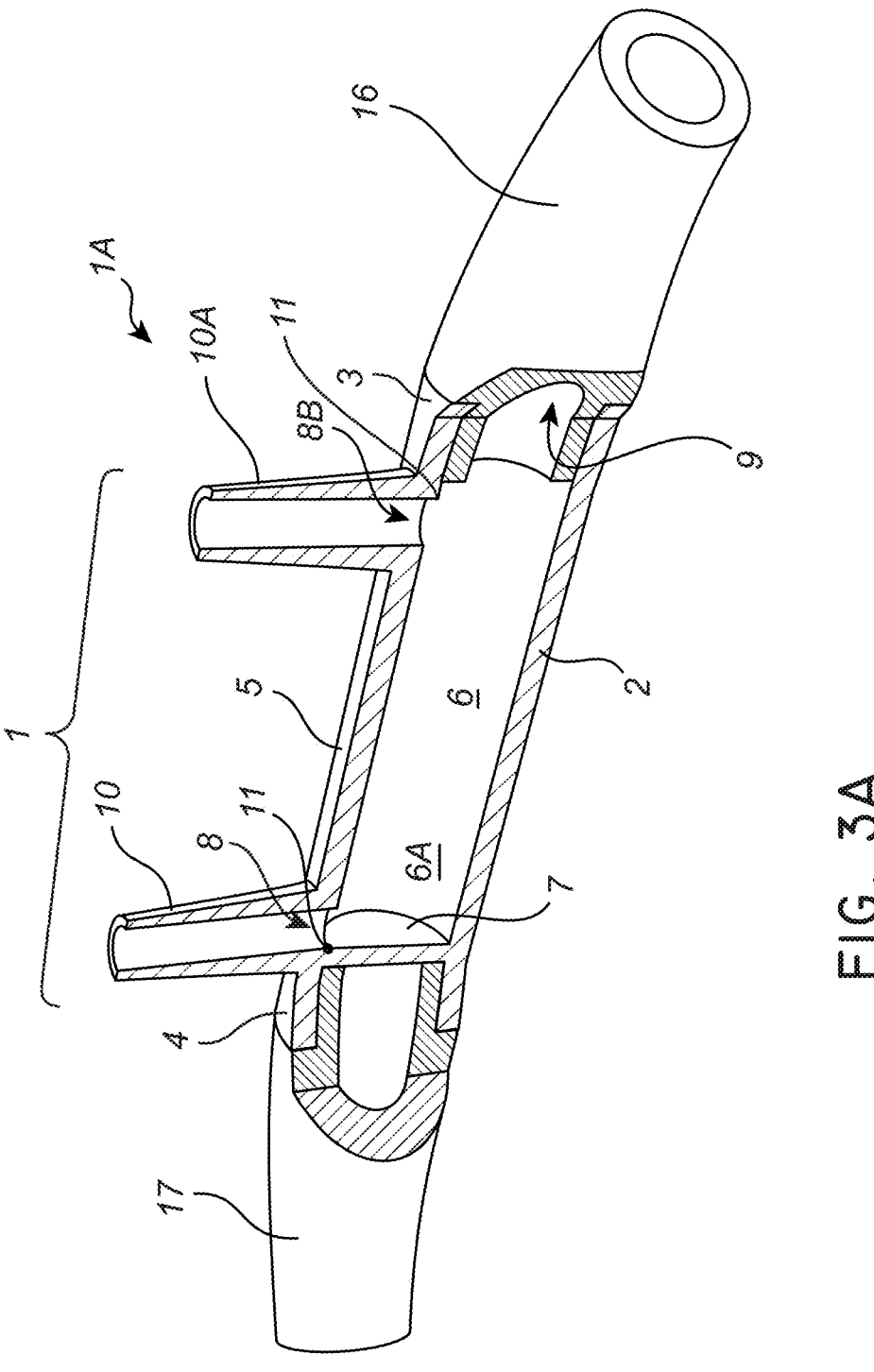
FIG. 3A shows a cutaway view of an additional embodiment of a cannula configured to collect exhaled gases from both nostrils of a patient.

FIG. 3A depicts an embodiment of a cannula system 1A configured to collect the exhaled gas from both of a patient's nostrils. The cannula 1 comprises an elongated tubular body 2 for the collection of gases exhaled through the first and second nostrils (not shown) of a patient. The tubular body 2 has a first and a second end portion 3, 4. The first end portion 3 defines an exit port 9 for exhaled gases. The exhaled gases enter the tubular body 2 via an inlet 8 and a first additional inlet 8A formed as holes extending through surface 5 of the tubular body 2. The tubular body is preferably essentially cylindrical and has a length L, where the inlet 8 is arranged at a distance of more than L/2 from said first end portion 3, such as in proximity to the second end portion 4, and the first additional inlet 8A is arranged at a distance of less than L/2 from said first end portion 3, such as in proximity to the first end portion 3. Thereby, the inlet 8 is adapted to receive exhaled gases from the second nostril of a patient, and the first additional inlet 8A is adapted to receive exhaled gases from the first nostril of a patient.

Thus, gases exhaled by the patient through the second nostril enter the cannula through the inlet 8 and gases exhaled by the patient through the first nostril enter the cannula through the first additional inlet 8A. The exhaled gases exit the cannula through the exit port 9. Although the cannula 1 is illustrated with nozzle 17, in some embodiments nozzle 17 may be omitted due to the positioning of the wall 7 such that gases cannot be received into the cannula 1 through nozzle 17. In some embodiments, nozzle 17 may be replaced with a cap or an attachment for a securing device used to secure the cannula 1 to the patient. In some embodiments, nozzle 17 may be included, as illustrated, and connected to extension tubing for use in securing the cannula 1 to the patient even though no therapeutic gases are delivered through the extension tubing or nozzle 17.

Preferably, the inlet 8 and additional inlet 8A comprise hollow prongs 10, 10A. The prongs 10, 10A are configured for insertion into a patient's nostrils and are further configured to allow fluid communication into the subvolume 6A of the tubular body 2. The hollow prongs 10, 10A are preferably molded integrally with the tubular body; however, the hollow prongs 10, 10A may alternatively be sealingly adhered to the tubular body by other means, including by use of an adhesive composition.

A wall 7 is internally disposed within the tubular body 2 in order to define a first subvolume 6A of the tubular body 2 into which exhaled gases are introduced. The first subvolume is arranged in the lengthwise direction toward the first end portion 3 of the tubular body 2.

The wall 7 is arranged adjacent to the inlet 8. Again, "adjacent" to the inlet 8 signifies that the wall 7 is arranged in immediate or near-immediate contact with the opening 8 so that no, or acceptably low, void volume is created between the wall 7 and the inlet 8. When the opening 8 comprises a hollow prong 10, the wall 7 can be seen to constitute an extension of an inner side of the hollow prong 10A from the tangential point 11 where the hollow prong 10A is joined with the inner side of the tubular body 2. For example, the wall 7 can be directly adjacent to the inlet 8 or within an acceptable range. For example, the range can be 0.0 to 0.5 mm; 0.0 to 1.0 mm; 0.0 to 2.0 mm, or anywhere in between. In an embodiment, the wall 7 is placed closer to the inlet 8 than the outlet 13.

The wall 7 thereby provides for an uninterrupted flow path for the exhaled gases from the inlets 8, 8A to the exit port 9, and essentially the entire subvolume 6A forms part of the flow path. Thus, gases exhaled by the patient through the first and second nostrils enter the cannula through the inlets 8, 8A and exit the cannula through the exit port 9 without any substantial interruption, turbulence, or back flow.

Figure 3B:
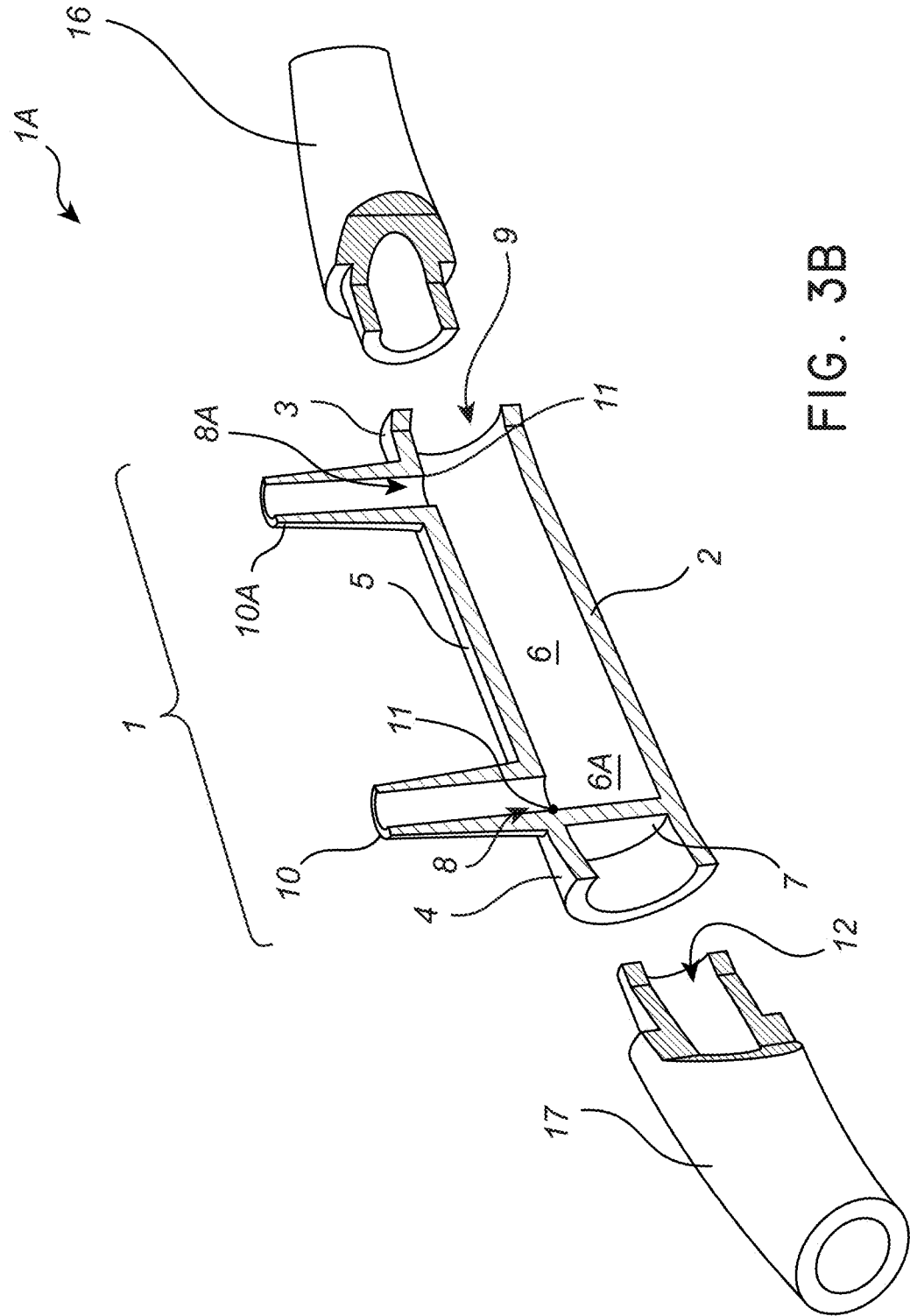
FIG. 3B shows an exploded view of the embodiment of FIG. 3A producible with the methods as described herein.

FIG. 3B illustrates an exploded view of the components of the cannula system 1A embodied in FIG. 3A. As illustrated, the cannula 1 and nozzles 16, 17 can be separately manufactured, for example by injection molding. These separate components can be assembled by solvent bonding. For example, an inserting end of nozzle 16 can be sized to fit within exit port 9. An exterior surface of the inserting end of nozzle 16 may be coated or provided with a solvent for solvent bonding and then inserted into exit port 9. Similarly, inserting end of nozzle 17 can be sized to fit within an entrance port 12. An exterior surface of the inserting end of nozzle 17 may be coated or provided with a solvent for solvent bonding and then inserted into entrance port 12. In alternative embodiments these components may be configured for a substantially fluid-tight press fit.

Figure 4A:
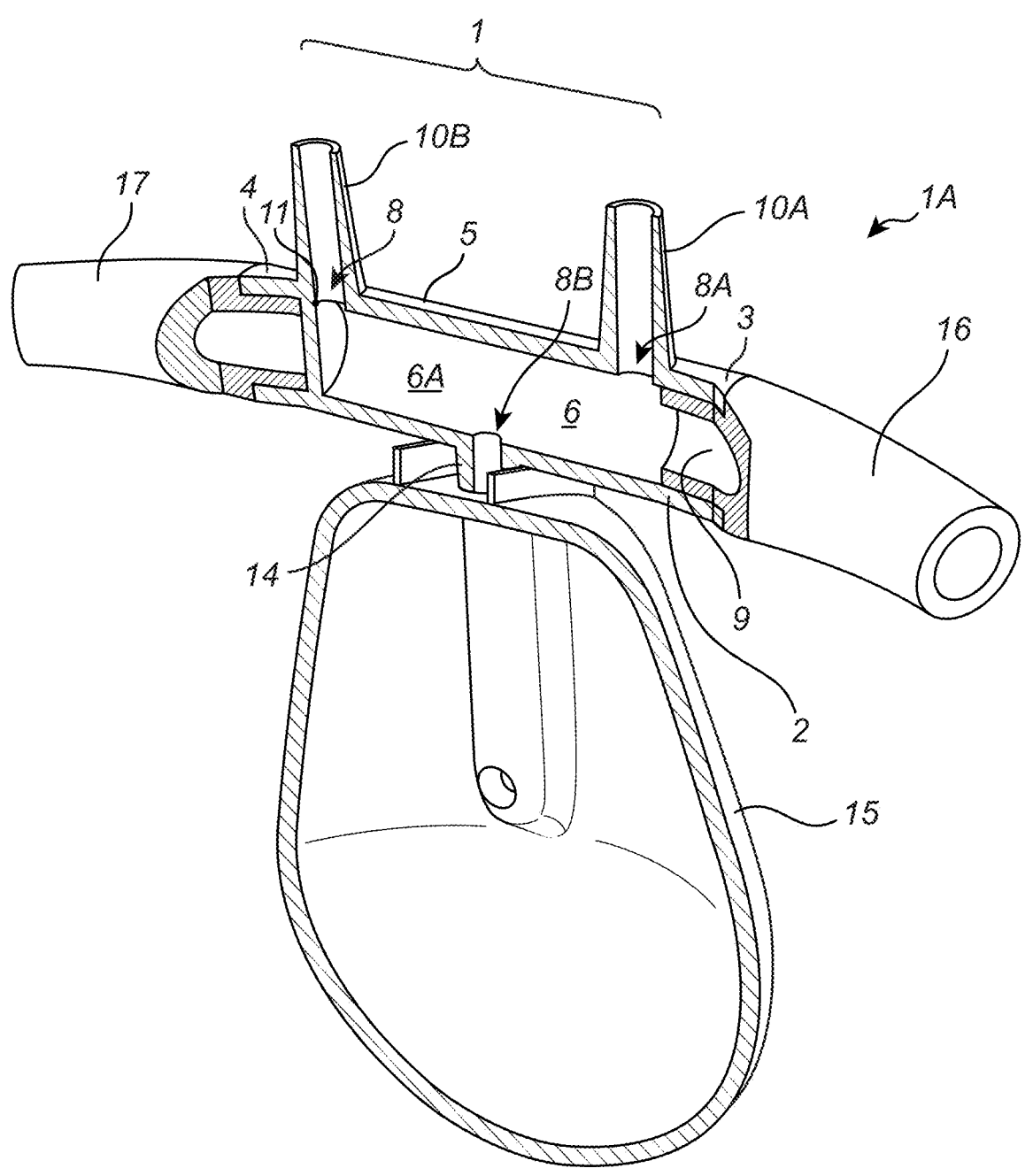
FIG. 4A shows a cutaway view of an additional embodiment of a cannula configured for the collection of exhaled gases from both nostrils of a patient and the collection of exhaled gases from the mouth of a patient.

FIG. 4A depicts an embodiment of a cannula system 1A configured to collect exhaled gas from both nostrils of a patient, as well as from the patient's mouth. This embodiment is similar to that discussed above with reference to FIGS. 3A and 3B but it also comprises a second additional inlet 8B, also formed as a hole extending through said surface 5, as seen in FIG. 4A. The second additional inlet 8B is arranged at a distance of about L/2 from said first end portion 3, such as substantially between the first and second end portions 3, 4. Additionally, the second inlet 8B is generally disposed on the cannula 1 opposite the inlet 8 and first additional inlet 8A. In other words, if the inlet 8 and first additional inlet 8A are disposed on the top of the cannula 1, the second additional inlet 8B will be disposed on the bottom. The second additional inlet 8B is thereby adapted to receive exhaled gases from the mouth of a patient.

The second additional inlet 8B preferably comprises a hollow prong 14, which allows for fluid communication into the subvolume 6A of the tubular body 2. An oral breath collector 15, a so-called "scoop," may be connected to the hollow prong 14 and configured to cover the mouth of a patient using the cannula system 1A. Thus, gases exhaled by the patient through the nostrils enter the cannula through the inlet 8 and the first additional inlet 8A, and gases exhaled by the patient through the mouth enter the cannula through the second additional inlet 8B. The exhaled gases exit the cannula through the exit port 9 and first nozzle 16.

As described above with respect to the embodiment of FIG. 3A, though the embodiment of FIG. 4A is illustrated with a second nozzle 17, in some embodiments nozzle 17 may be omitted or replaced with a cap, other attachment, or securing device used to secure the cannula 1 to the patient. In some embodiments, nozzle 17 may be included, as illustrated, and connected to extension tubing for use in securing the cannula 1 to the patient even though no therapeutic gases are delivered through the extension tubing or nozzle 17.

Figure 4B:
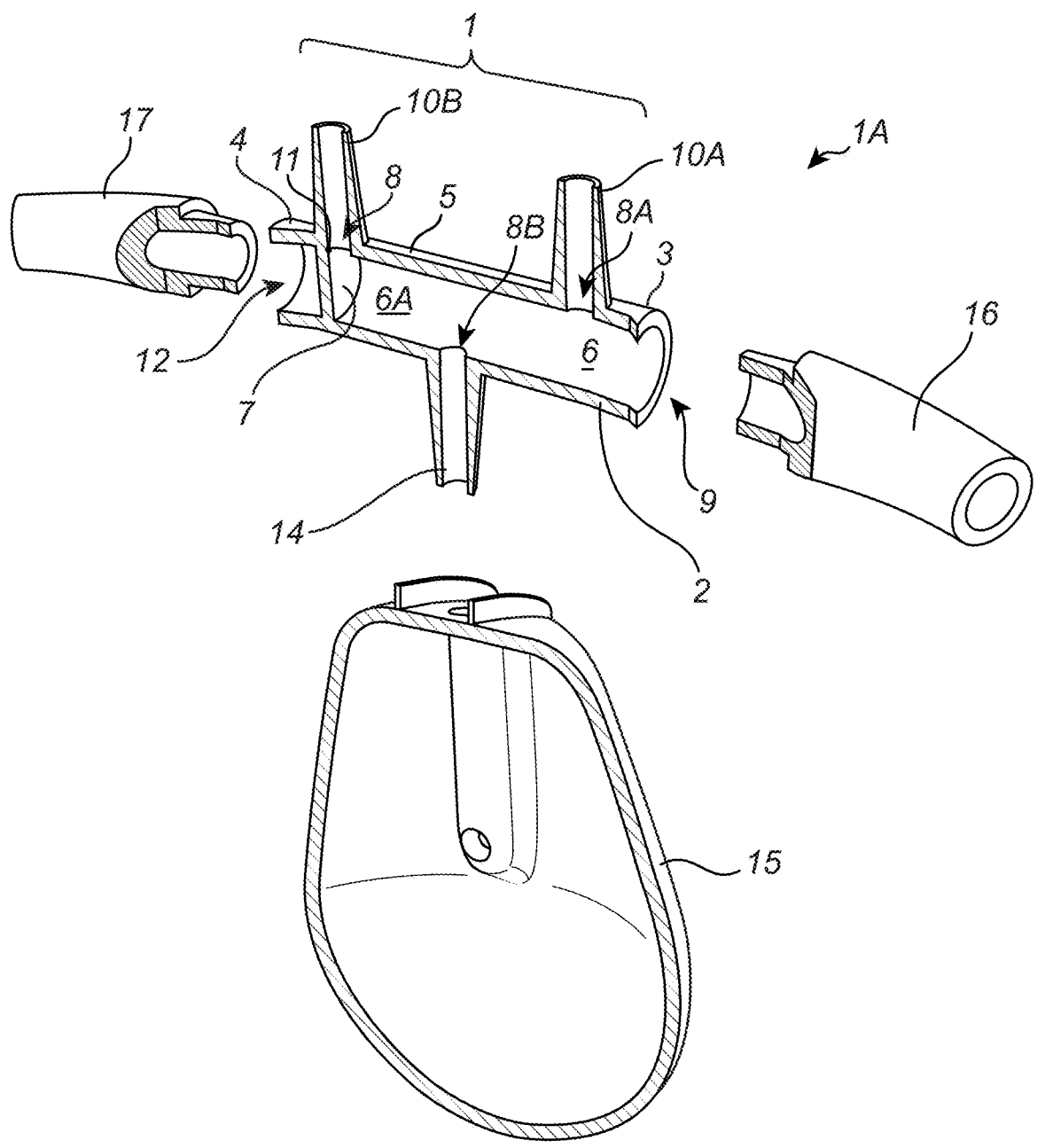
FIG. 4B shows an exploded view of the embodiment of FIG. 4A producible with the methods as described herein.

FIG. 4B illustrates an exploded view of the components of the cannula system 1A embodied in FIG. 4A. As illustrated, the cannula 1 and nozzles 16, 17 can be separately manufactured, for example by injection molding. These separate components can then be assembled by solvent bonding. For example, an inserting end of nozzle 16 can be sized to fit within exit port 9. An exterior surface of the inserting end of nozzle 16 may be coated or provided with a solvent for solvent bonding and then inserted into exit port 9. Similarly, inserting end of nozzle 17 can be sized to fit within an entrance port 12. An exterior surface of the inserting end of nozzle 17 may be coated or provided with a solvent for solvent bonding and then inserted into entrance port 12. An aperture in the top of the oral breath collector 15 can be sized to receive hollow prong 14, and the breath collector may include a portion on the interior of the breath collector that extends around hollow prong 14 once inserted. An exterior surface of the prong 14 can be coated or provided with solvent for solvent bonding and then inserted into the aperture of the oral breath collector 15. In alternative embodiments these components may be configured for a substantially fluid-tight press fit.

Figure 5:
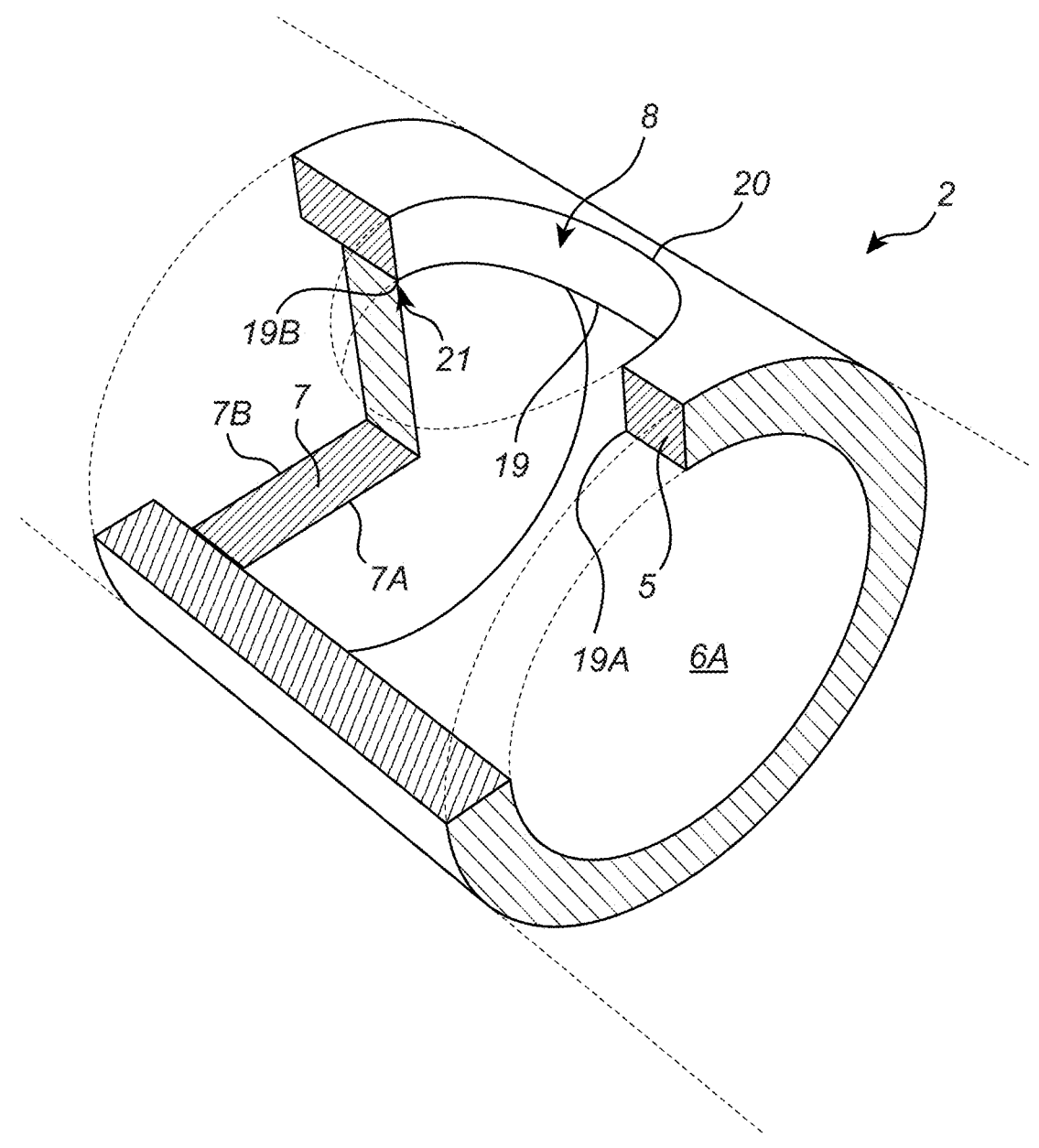
FIG. 5 shows a detailed cut away view of an exemplary arrangement of a portion of a cannula configured with a wall adjacent to an inlet.

FIG. 5 depicts a cutaway detail view of a portion of a tubular body 2 of a cannula comprising a wall 7 and an inlet 8. FIG. 5 may be illustrative of a portion of each of the embodiments shown in FIGS. 1A-4B. The wall 7 is arranged adjacent to the inlet 8, such that the exhaled gases can generally only move in a single direction, towards the exit port 9, upon entering the tubular body 2 of the cannula. Accordingly, this positioning of the wall 7 substantially eliminates any void volume within the tubular body 2.

The wall 7 is internally disposed within the tubular body 2 such that the entire periphery of the wall 7 sealingly engages the inner surface of the tubular body 2 to form a gas-tight seal. The wall 7 is preferably molded integrally with the tubular body 2; however, in some embodiments, the wall 7 may alternatively be sealingly adhered to the tubular body 2 by other means such as with an adhesive composition.

With reference to FIG. 5, the inlet 8 is configured as a hole extending through the surface 5 and generally forms a cylindrical volume; however, it may alternatively form, for example, a conical, square, or rectangular volume. The end of the inlet 8 on the inner side of the tubular body 2 comprises a first perimeter 19 facing the subvolume 6A, and the end of the inlet facing the outer side of the tubular body 2 comprises a second perimeter 20 facing the source of exhaled gases.

The first perimeter 19 has a first edge 19A facing the first end portion of the tubular body 2, and a second edge 19B facing the second end portion of the tubular body 2 (end portions are not shown in FIG. 5). When the inlet 8 forms a cylindrical volume, the perimeter 19 is essentially circular, and the first and second edges 19A, 19B constitute points on the perimeter 19. When the opening forms, for example, a square volume, the perimeter 19 is essentially square, and the first and second edges 19A, 19B may constitute opposite sides of said square, or, alternatively, points in opposite corners of the square.

The wall 7 has a first side 7A facing the first end portion of the tubular body 2 and a second side 7B facing the second end portion of the tubular body 2 (end portions are not shown in FIG. 5).

The wall 7 is arranged adjacent to said inlet 8, meaning that the first side 7A of the wall 7 extends from a point 21 arranged in close vicinity to, or in contact with, said second edge 19B of the perimeter 19. Preferably, the distance from the second edge 19B to the point 21 is less than 1.0 mm, more preferably less than 0.5 mm, and most preferably 0.0 mm.

As stated above, and as illustrated in FIGS. 1A-4B, when the inlet 8 comprises a hollow prong 10, 14 the wall 7 can be seen to constitute an extension of an inner side of the hollow prong 10, 14 from the tangential point 11, 18 where the hollow prong 10, 14 is joined with the inner side of the tubular body 2. In this case, the tangential point 11, 18 in FIGS. 1A-4B corresponds to the point 21 in FIG. 5, and reflects the case where the point 21 is in contact with the second edge 19B of the perimeter 19.

The wall 7 is preferably substantially perpendicularly arranged within the tubular body 2. However, the wall 7 may also have an inclination within the tubular body 2, or it may have a curved shape, adapted to provide a smooth, laminar flow of gases from the inlets 8, 8A 8B to the outlet 9. Thus, the wall 7 may be constructed in several different ways, as long as substantially no void volume for the gas flow is created within the subvolume 6A.

Various differing embodiments, according to the principles of the present disclosure, of a cannula and cannula system have been described above with reference to FIGS. 1A through 5. The various embodiments, however, may have some common general characteristics, which may be adjusted as required. Some of these general characteristics will now be described. Reference numerals refer to like elements as shown in each of FIGS. 1A-5.

In preferred embodiments, the tubular body 2 is essentially cylindrical in shape and has a length L extending between the first and second end portions of the tubular body. The expression "essentially cylindrical" is meant to signify that the tubular body has the geometrical shape of a cylinder; however, it also encompasses the case when the entire the tubular body or a portion thereof is curved or bent. The tubular body may also comprise other geometric shapes, for example a conical or rectangular shape.

The wall 7 generally divides the internal volume 6 of the tubular body 2 into a first subvolume 6A and a second subvolume 6B. However, the present disclosure also encompasses the case when the first subvolume constitutes the entire internal volume 6, that is, the wall 7 is located at the second end 4 of the tubular body.

When an inlet 8, 8A, 8B or an outlet 13 comprises a hollow prong 10, 10A, 10B, 14, it is preferred that the hollow prong has a conical shape and is arranged to protrude essentially perpendicularly from the tubular body 2 (as seen in any of FIGS. 1A-4B). However, it is also contemplated that a hollow prong 10, 10A, 10', 14 may have different geometric shape, as long as fluid communication through the hollow prong 10, 10A, 10B is allowed. Preferably, the interior volume of the hollow prong 10, 10A, 10B, 14 is in the form of a cylinder.

The cannula 1, including the hollow prongs 10, 10A, 10B, 14 and the wall 7, is preferably manufactured by injection molding of polyvinyl chloride (PVC) or polyurethane (PU).

When the cannula 1 contains two hollow prongs to be arranged in both nostrils of a patient, different sizes of the cannula 1 may be manufactured depending on whether the cannula is intended to be used for adults, children or infants. A suitable distance between the prongs on a cannula for adults is about 16 mm, a suitable distance between the prongs on a cannula for children is about 12 mm, and a suitable distance between the prongs on a cannula for infants is about 9 mm. If applicable, the size of the oral breath collector 15 and its position in relation to the prongs may likewise be adapted depending on whether it is intended to be used for adults, children or infants. In certain circumstances, in which a patient has trouble exhaling through the nose or prefers exhaling through the mouth, provision of the scoop 15 with the nasal cannula 1 can enable collection of larger quantities of exhaled gases from such a patient compared to use of a nasal cannula without a scoop.

Exhaled gases collected from the nostrils and/or mouth of a patient are led into the inlets 8, 8A, 8B through hollow prongs 10, 10A, 14. However, other constructions may be contemplated, for example exhaled gases collected from the nostrils or mouth of a patient may be led into the inlets 8, 8A, 8B through flexible tubes or apertures extending through the surface of the tubular body.

The interior diameter of a tubular body 2 for use in a cannula 1 suitably lies in the range of about 2-4 mm, and preferably is about 3 mm. When a cannula is designed to comprise two or more inlets for collecting exhaled gases, it is advantageous to employ a tubular body 2 having diameter in the lower end of the range, such as in the range of about 2-3 mm. The present inventors have surprisingly found that a smaller diameter of the tubular body 2, in combination with placing a wall in direct connection to the inlet 8 which is located at the farthest distance from the point where the gases exit the cannula, further adds to the effect of obtaining a very high accuracy in the analysis of exhaled gases.

When the cannula provides for the supplementation of a treating gas, for example oxygen, to the respiratory system of a patient, the treating gas may enter the respiratory system via the mouth and/or one or both nostrils of a patient. Preferably, the treating gas is supplied through a hollow prong to a nostril of a patient. However, the supplementation of a treating gas may also be effected, for example, by providing an aperture in the tubular body near the nostril of the patient. In addition, a treating gas may be supplemented to the mouth of a patient, for example via an additional hollow prong or via an aperture in the tubular body near the mouth of a patient.

For embodiments that relate to the simultaneous supplementation of a treating gas, a first nozzle 16 is adapted for the transport of exhaled gases from the cannula, and a second nozzle 17 is adapted for the supplementation of a treating gas to the cannula. The first nozzle 16 is generally adapted for a flow of about 50 ml/min, while the second nozzle 17 is generally adapted for a flow of up to 5 liters per minute. The first nozzle 16 is generally connected via an extension tube (not shown) to conventional analyzing means for analyzing at least one component (for example $CO_2$) of the exhaled gases. The second nozzle 17 is generally connected via an extension tube (not shown) to a conventional supply of a treating gas (for example oxygen or an anesthetic agent). Although in some embodiments, each nozzle may be configured for the same flow.

For embodiments that do not relate to the supplementation of a treating gas, the first nozzle 16 is adapted for the transport of exhaled gases from the cannula, while the second nozzle 17 may be adapted as required. For example, the second nozzle 17 may be of the same kind or of a different kind as the first nozzle 16. In some embodiments, the second nozzle 17 may be omitted. Additionally, in some embodiments that do not relate to the supplementation of a treating gas may lack the subvolume 6B the wall 7 is disposed at the second end portion 4 of the tubular body.

The nozzles are preferably manufactured by injection molding of polyvinyl chloride (PVC) or polyurethane (PU). The nozzles 16, 17 are preferably slightly curved, which allows for the alignment of extension tubes in a desired direction.

The present disclosure thus provides for a convenient way of providing several different constructions with a limited number of pieces.

As used herein, the term "cannula" in its most general form refers to the elongated tubular body, including an inlet and a wall internally disposed within the tubular body. In various embodiments, the cannula may additionally comprise one or more additional inlets and/or outlets, as well as two or more prongs.

As used herein, the term "cannula system" refers to the cannula as defined above, in combination with at least one nozzle, and optionally, may additionally include at least one extension tube, such as a sampling tube or a treating gas tube.

The nasal/oral cannula can be used in a nasal/oral cannula system 1A incorporating the Nomoline™ sampling line provided by Masimo, as described in more detail below.

Figure 6:
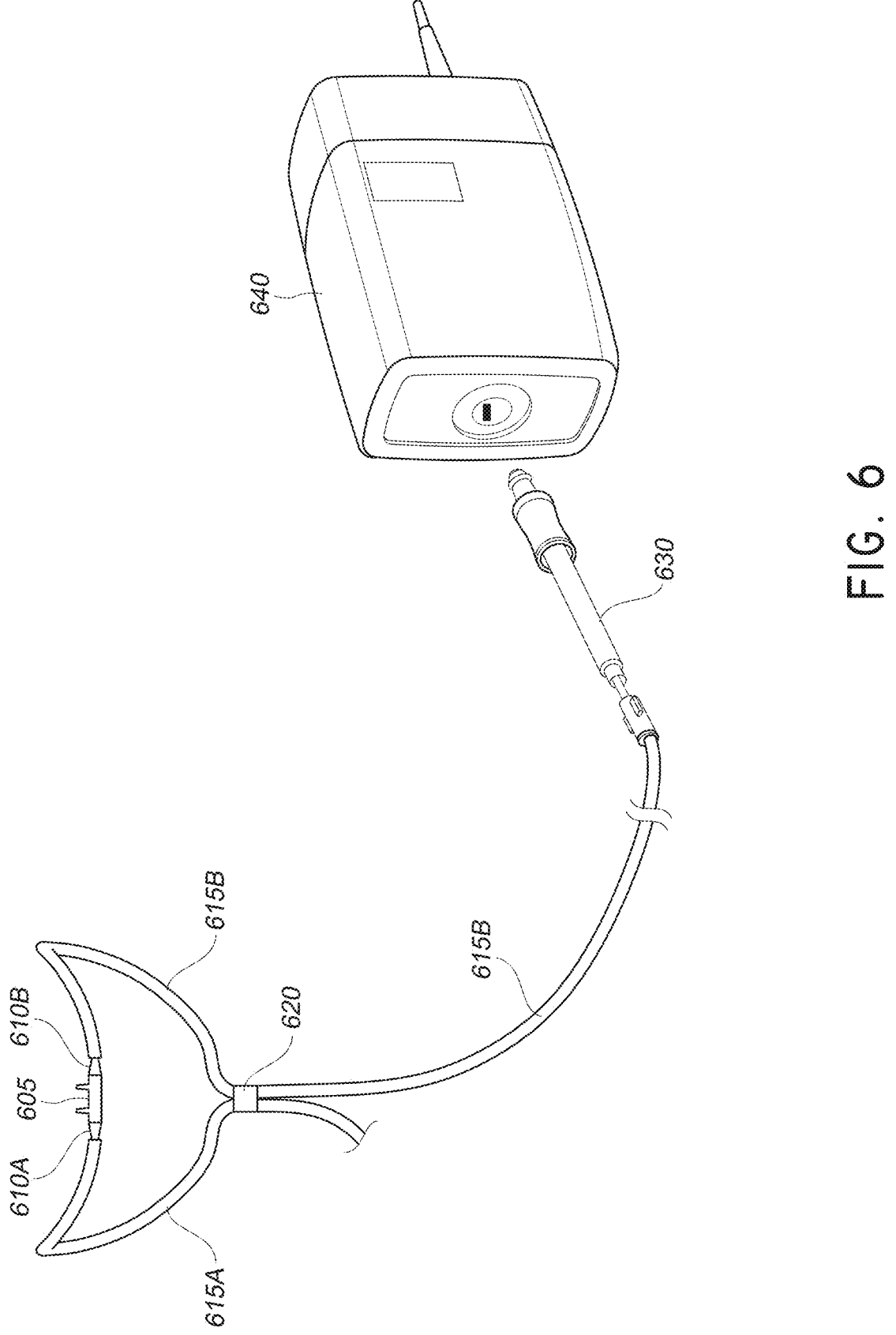
FIG. 6 illustrates an embodiment of a gas sampling system implementing an embodiment of a cannulae described herein.

FIG. 6 illustrates an embodiment of a gas sampling system implementing an embodiment of a cannula described herein.

The cannula 605 can include prongs for placement in a patient's nostrils and, though not shown, in some embodiments can include an additional prong coupled to an oral breath collector. The cannula 605 can have any of the internal wall placements described above for provision of therapeutic gases and/or collection of exhaled gases from one or both nostrils. The cannula may be secured to one or both of nozzles 610A, 610B depending upon the placement of wall and the design of the system for securing to a patient. As illustrated, a first section of extension tubing 615A, 615B is in fluid communication with and extends from each of nozzles 610A, 610B in a direction to pass over the cars of a patient and then be secured using slide bolo 620 under the chin of a patient. It will be appreciated that other known securing techniques can be implemented with the cannula 605. Extension tubing 615A can be used in some examples for provision of therapeutic gases through nozzle 610A and an outlet of cannula 605 to a first nostril of a patient. Extension tubing 615B can be used to receive exhaled gases from one or both nostrils of the patient via cannula 605, prong(s), and nozzle 610B.

In some embodiments, extension tubing 615B can be coupled to a sampling line 630, for example, the Nomo-line™ sampling line provided by Masimo. Water vapor within the sampled exhaled gases of a patient can naturally condense within the respiratory circuit, as well as within the sample tubing of the gas analyzer 640. If allowed to reach the gas analyzer sample cell, the condensate can affect measurement accuracy and/or permanently damage the instrument. In order to protect the gas analyzer 640 from the effects of condensed water, patient secretions, and bacterial contamination, sampling line 630 can be provided between the patient and the gas analyzer 640. The sampling line 630 can allow water in the exhaled gases to evaporate into the surrounding air, while leaving the oxygen, carbon dioxide, and/or anesthetic or other gases to be measured unaffected. Exhaled gases can enter the sampling line 630 from the extension tubing 615B. As the exhaled gases pass through the sampling line 630, a polymer can absorb water from the patient's gas sample and evaporate it into surrounding air. The remaining gas sample can be passed through a filter that substantially blocks the passage of water and/or bacteria while permitting passage of exhaled gases and any thera-peutic agents in the exhaled gases. In other embodiments the sampling line 630 can be omitted, and the extension tubing 615B can be coupled directly to a gas analyzer 640.

Gas analyzer 640 can receive exhaled gases from the sampling line 630 (or directly from the extension tubing 615B) and analyze the exhaled gases, for example to deter-mine various gas concentrations. Gas analyzer 640 can be a sidestream gas analyzer available from Masimo Corporation of Irvine, CA, for example an ISA™ Sidestream Analyzer. Although discussed primarily herein in the context of $CO_2$, gas analyzer 640 can be configured for measuring other gas concentrations and/or patient parameters, for example res-piration rate.

FIG. 7A illustrates a block diagram of one embodiment of a nasal cannula kit 710. The kit 710 includes one or more preassembled cannula(e) with nozzles 712, one or more preassembled cannula(e) with nozzles and an oral breath collector 714, extension tubing 716, and securement device 718. In some examples, cannula 712, 714 with varying internal wall positionings can be provided in a single kit and labeled such that a clinician can select the cannula appro-priate for a current patient need. In some examples, all cannulae 712, 714 within a kit may have the same internal wall positioning. Some embodiments of kit 710 may include just one type of preassembled cannula(e) with nozzles 712 and preassembled cannula(e) with nozzles and an oral breath collector 714. The number and type of separate sections of extension tubing 716 can correspond to the number of nozzles on all of the cannulae 712, 714 included in the kit 710 and to the internal wall positioning of the cannulae 712, 714. Similarly, the type and number of securement devices 718 can correspond to the types and number of cannula 712, 714 included in the kit 710, as well as to the sizes of the cannulae 712, 714 (for example, adult sized cannula versus infant sized cannula) and/or intended uses of the cannulae 712, 714 (for example, for mobile patients or immobilized patients). The kit 710 can be packaged as a sterile kit, for example using sterilized trays and/or blister packs, and may provide individual components in separately-accessible ster-ilized compartments.

Figure 7B:
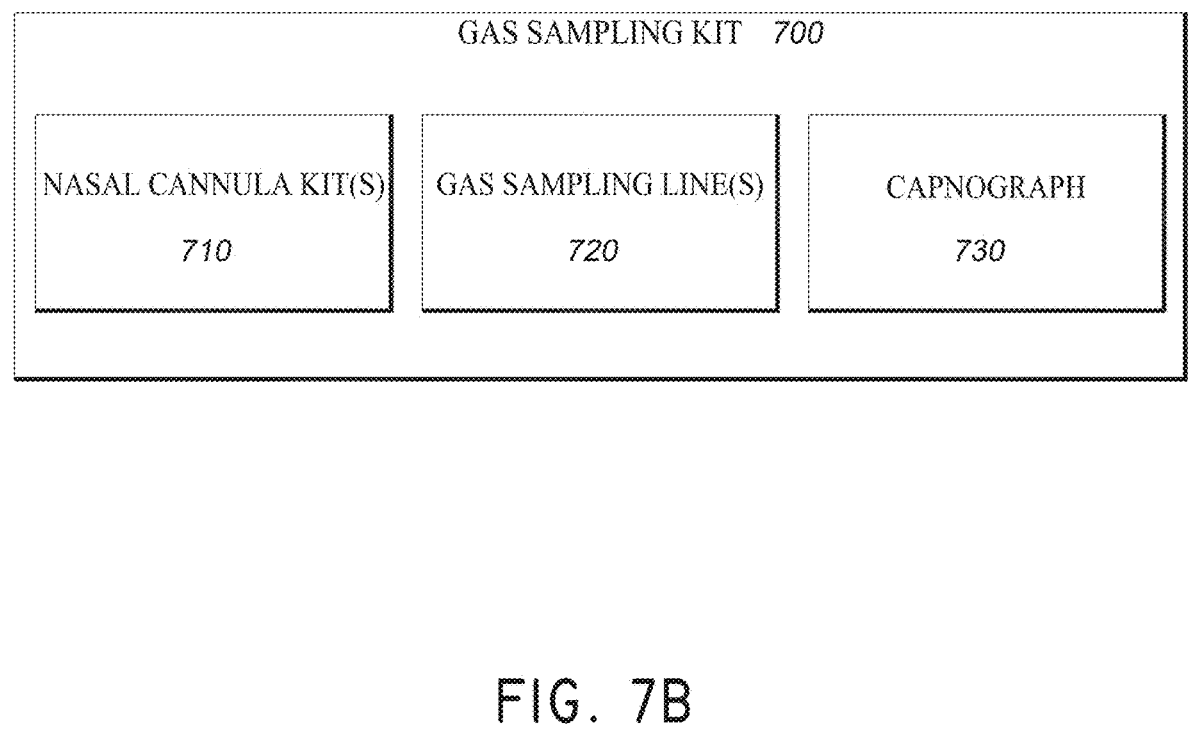

FIG. 7B illustrates a block diagram of one embodiment of a gas sampling kit 700. The gas sampling kit 700 can include one or more nasal cannula kits 710 as described above, one or more gas sampling lines 720, and one or more capno-graphs 730. An example of a gas sampling line 720 is Nomoline™ available from Masimo, and an example of a capnograph 730 is an ISA™ Sidestream Analyzer available from Masimo. In some embodiments, gas sampling lines 720 may not be reusable and a gas sampling line 720 can be provided for each cannula in the nasal cannula kits 710. Gas sampling lines 720 may be provided in individually-acces-sible sterilized packaging, for example a blister pack or sterilized tray. In some embodiments, the capnograph 730 may be reusable and a kit 700 may include a single capno-graph 730.

Figure 8A:
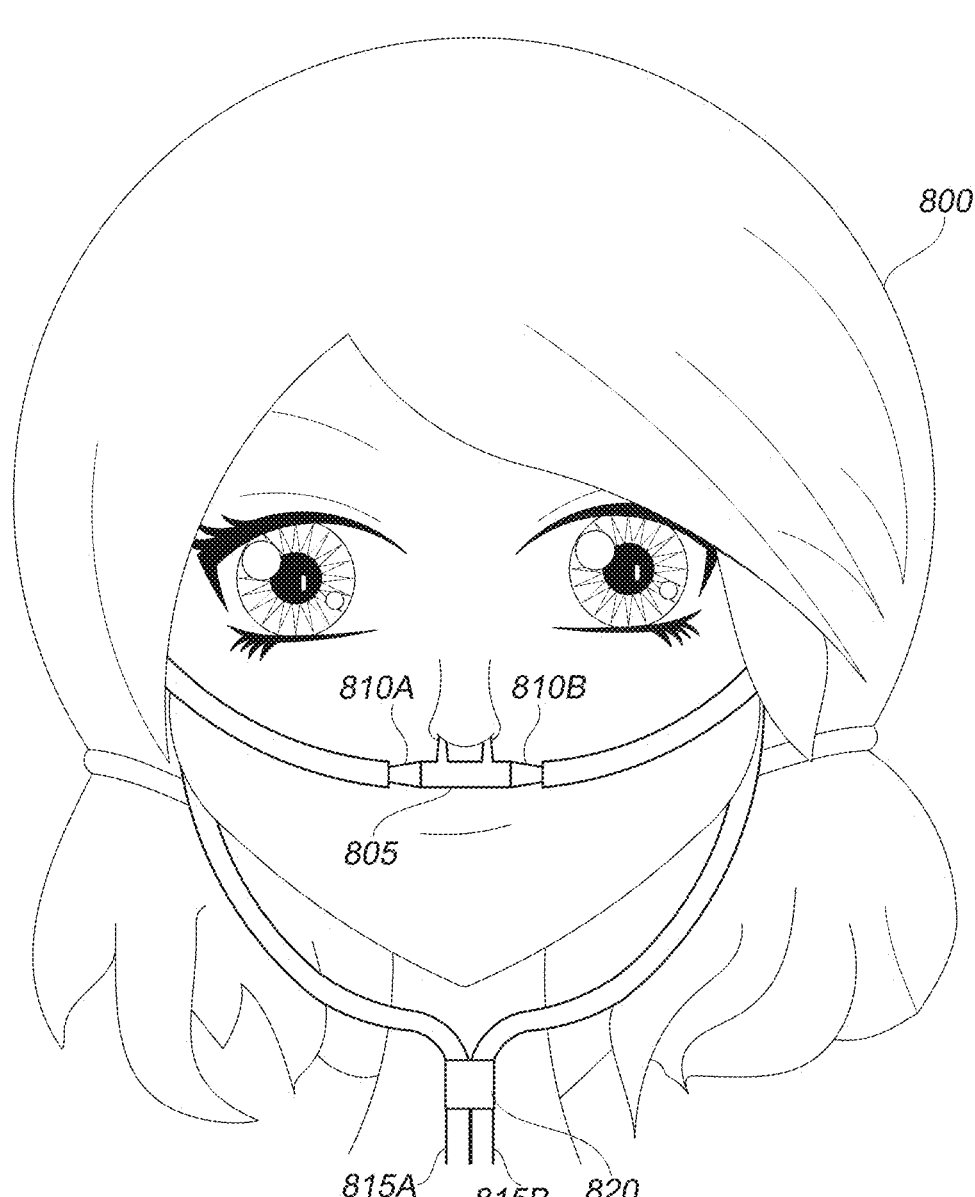
FIG. 8A illustrates an example positioning of an embodiment of a cannula on a patient.

FIG. 8A illustrates an example positioning of an embodi-ment of a cannula 805 on a patient 800. As illustrated, the prongs of cannula 805 are positioned in the patient's nostrils and a nozzle 810A, 810B is coupled to each side of the cannula 805. Extension tubing 815A, 815B is each in fluid communication with one of nozzles 810A, 810B, extending over the ears of the patient 800 and then downward under the chin of the patient 800 to be secured by slide bolo 820. Accordingly, the prongs of the cannula 805 are substantially fixed in position in the nostrils of the patient 800.

The illustrated manner of securing cannula 805 to patient 800 represents one of many available suitable securing manners known in the art. In other embodiments, an elastic strap may be provided to secure the cannula 805 to the patient 800, the extension tubing 815A, 815B may pass over and/or behind the head of patient 800, or the extension tubing 815A, 815B may be secured to the cheeks of the patient's face. In some examples only a single nozzle 810B may be used (for example, where the cannula 805 includes an internal wall positioned to collect exhaled gases from both nostrils of the patient 800 or in other uses in which no therapeutic gas is provided) and accordingly extension tub-ing 815A may be omitted and a single-sided securing technique can be used to fix the prongs of the cannula 805 in the nostrils of the patient 800.

Figure 8B:
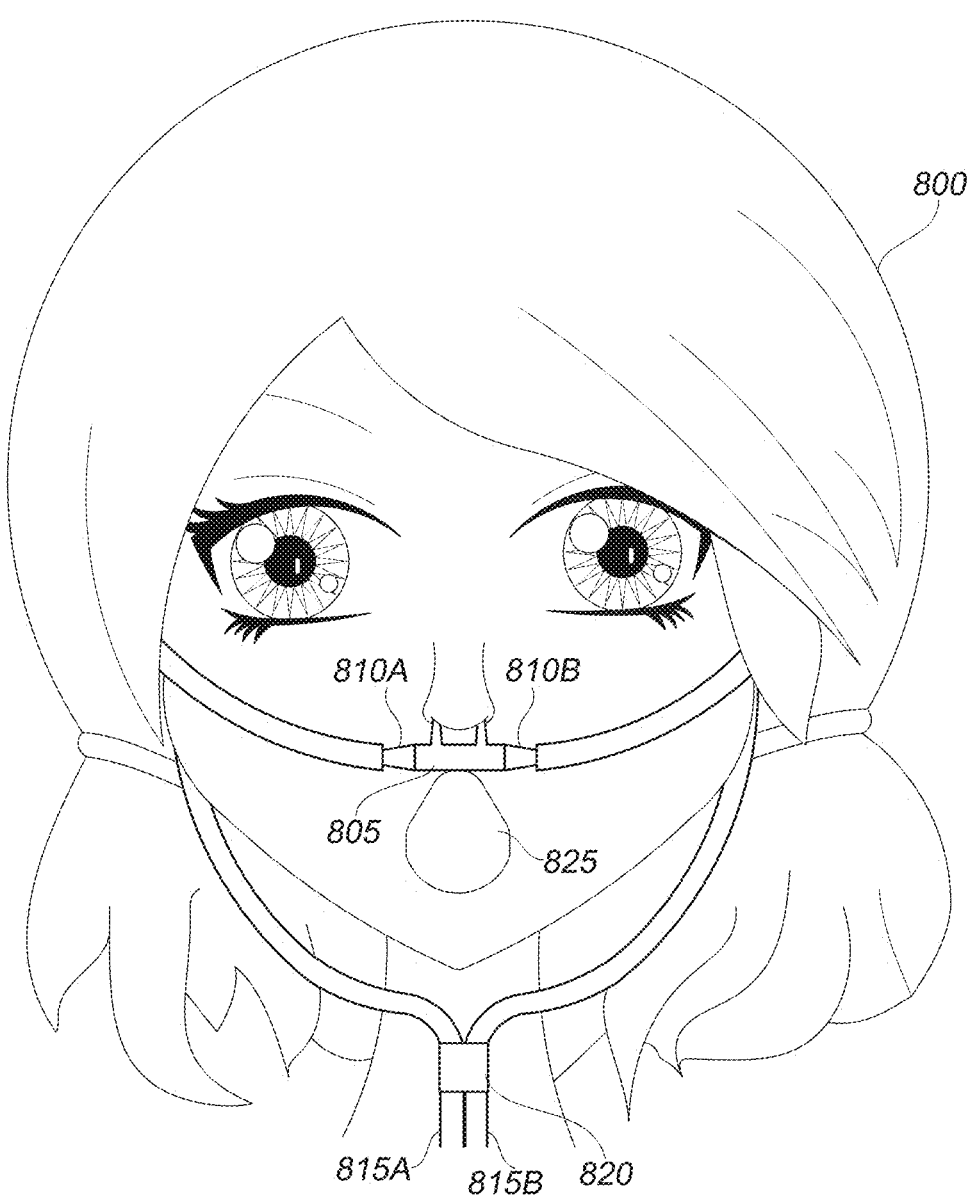
FIG. 8B illustrates an example positioning of another embodiment of a cannula on a patient.

FIG. 8B illustrates an example positioning of another embodiment of a cannula 805 on a patient 800. As illus-trated, the cannula 805 includes an oral breath collector 825 positioned over the mouth of the patient 800. The illustrated scale between the oral breath collector 825 and the patient 800 represents one embodiment, and larger or smaller breath collectors 825 can be used depending on the size of the patient and other design requirements.

The various embodiments of cannulae as described herein, some of which are depicted in FIGS. 1A-4B may advantageously be manufactured according to the methods described herein below. These methods provide for a very convenient and efficient way of achieving the different cannulae and nozzles described above.

In one embodiment of the method, the modules of a cannula system are injection molded separately and then assembled by solvent bonding. Injection molding is a manu-facturing process for producing parts by injecting manufac-turing material in a liquid state into a mold and allowing it to cool and harden. In the manufacturing of a cannula system in accordance with the techniques described herein, different molds shaped in desired designs are therefore provided. The molds generally consist of two components, that, when assembled with relevant cavity tools, form a cavity corresponding to the desired design. Manufacturing material enters the mold through an opening that allows the material to flow into the mold.

In the research work leading to the cannula manufacturing systems and techniques described herein, it was found that the combination of injection molding and solvent bonding provides for a very convenient procedure for manufacturing a nasal/oral cannula system. In particular, the use of solvent bonding for assembling the pieces leads to very smooth boundaries between the components of the cannula system, which is advantageous for maintaining a smooth, laminar flow of gases through the system. The disclosed manufacturing methods provide for a cannula system which, from a comfort point of view, is as good as, or better than, a cannula system produced by conventional dip molding, while providing all the advantages associated with injection molding.

The manufacturing of an embodiment of cannula in accordance with FIGS. 1A and 1B will now be described in further detail with reference to FIG. 9A, which shows an exploded perspective view a cannula mold and corresponding inserts and pins. Reference numbers not shown in FIG. 9A correspond to elements of the embodiment of a cannula shown in FIGS. 1A and 1B. Those of skill in the art will understand that the mold and manufacturing principles disclosed herein may be modified and applied for the manufacturing of other embodiments of cannulae (for example, the embodiments depicted in FIGS. 2A-4B).

A mold 100 for injection molding a nasal/oral cannula 1 comprises a first and a second mold body element 101, 102. The first mold body element 101 has a first end surface 103 and a second end surface 104, three side surfaces 105 and a contact surface 106. The second mold body element 102 similarly has a first end surface 107 and a second end surface 108, three side surfaces 109, and a contact surface 110. The contact surfaces 106 and 110 of the mold body elements 101 and 102 are intended to be arranged facing towards each other when the mold is arranged in a molding position. The mold is divided in at least two body elements to make it possible to open the mold and remove the injection molded cannula. The first and second mold body elements 101, 102 have substantially the same cuboidal shape so as to fit together when the mold is arranged in the molding position.

Within the mold, a cavity 111 is formed in the first and second mold body elements 101, 102. The cavity 111 is shaped to create a desired outer shape of the elongated tubular body 2 of the cannula 1. The cavity 111 is elongated in shape and extends along a substantially straight axis A arranged in the plane of the contact surfaces 106 and 110 of the mold body elements 101, 102 (when the mold body elements are placed into contact with each other, or, in other words, in the molding position) and parallel to the side surfaces 105, 109 of the cuboidal mold 100. The cavity has a substantially circular cross section and is ended by a first and a second end surface 112, 113 arranged transverse to the longitudinal axis A. One half of cavity 111 is disposed in the first mold body element 101 and the other half of cavity 111 is disposed in the second mold body element 101, such that when the mold body elements are brought into the molding position the entire cavity 111 is formed in substantially the shape of a cannula 1 to be formed.

A first elongated insert 114 having an inner end 115 facing the cavity 111 and an outer end 116 arranged outside the mold is configured to extend through an opening 117 in the first end wall 112 of the cavity. The shape of the opening 117 and the cross sectional shape of the first insert 114 may correspond to provide a sealing fit between the two components and prevent molding material from exiting the mold.

The first insert 114 may have a cross-sectional area smaller than the cross-sectional area of the cavity 111 so as to form a space within the cavity around the insert, i.e., the shape of the tubular body 2 of the casted cannula.

In the opposite end of the cavity 111 a second elongated insert 118 having an inner end 119 facing the cavity 111 and an outer end 120 arranged outside the mold may similarly be configured to extend through an opening 121 in the second end wall 113 of the cavity. The second insert 118 may also have a cross-sectional area smaller than the cross-sectional area of the cavity to form a space within the cavity around the insert. In some embodiments, the cross-sectional area of the second elongated insert 118 may be designed to match or substantially match a shape of the opening 121 to prevent leakage of injected molding material through the opening 121.

The first and second inserts 114, 118 are movably arranged in the openings 117, 121 in respective end walls of the cavity 111 between a molding position and a release position. In the molding position, the first and second inserts are arranged in the cavity with their inner ends facing each other (as shown in FIG. 9B). The inner ends are arranged at a distance from each other such that a space corresponding to the interior wall 7 of a cannula may be formed between the inner ends of the inserts once the molding material is supplied to the cavity. The respective inner ends of the inserts are generally designed to arrange the interior wall 7 of the cannula to be substantially perpendicularly disposed within the tubular body 2. However, as discussed above, the respective inner ends of the inserts may alternatively be designed to provide an inclined wall or a wall having a curved shaped.

In order to form the inlets and/or outlets 8, 13 in the surface 5 of the cannula 1, the mold furthermore may comprise a first insert pin 123 having a forward end 124 facing the cavity and an outer end 125 arranged outside the mold. The insert pin 123 is movably arranged in the mold between a molding position and a release position. In the molding position, the forward end 124 of the insert pin 123 is arranged in the cavity with the forward end 124 in contact with either the first or second insert 116, 119 to form an inlet/outlet 8, 13 in the surface 5 of the cannula 1 (as shown in FIG. 9B). In the release position, the insert pin 123 is retracted from the cavity to release the cannula from the mold (as shown in FIG. 9A). The mold furthermore comprises a second insert pin 126 which may be similar to the first insert pin 123, i.e., having a forward end 127 in the cavity and an outer end 128 outside the mold. The second insert pin 126 is disposed so as to be longitudinally separated from the first insert pin 123 to form a second inlet/outlet 8, 13 in the tubular body 2 of the cannula. The second insert pin 126 may extend along an axis B2 substantially parallel to the axial direction B1 of the first insert pin 123. The axes B1 and B2 extend substantially perpendicular to the longitudinal axis A of the cavity 111.

In an embodiment, the mold 100 comprises a first insert pin arranged to form an opening in the surface 5 of the tubular body 2 cannula 1. However, in the illustrated embodiment of FIGS. 9A and 9B, the mold 100 is designed for a cannula comprising two hollow prongs 10, 10B, and one inlet 8 and one outlet 13. These features are formed by the first and second prong recesses 130, 131 of mold 100, as well as first and second pin inserts 123, 126.

The first and second prong recesses 130, 131 extend coaxially with the first and second insert pins 123, 126. The first and second prong recesses 130, 131 have a larger cross sectional area than the first and second insert pins 123, 126 so as to form a space around the insert pins within the cavity 111. The first and second prong recesses 130, 131 may have a conical shape with larger cross sectional area close to the center of the cavity than in the area of the end surfaces. In some embodiments, the cross-sectional area of the first and second insert pins 123, 126 may be designed to match or substantially match a shape of the corresponding opening 132, 133 to prevent leakage of injected molding material.

The first and second insert pins 123,126 are movably arranged in corresponding openings 132, 133 in the first and second end surfaces 105, 190. The forward ends 124, 127 of the insert pins 123, 126 are generally designed to provide a tight seal against the first or second inserts 114, 118. For example, when the inserts 114, 118 have a cylindrical shape, the forward ends 124, 127 of the insert pins may have a concave design. The creation of a hollow passage in a hollow prong 10, 10A, 10B, 14 is thus independent of the outer design of the hollow prong 10, 10A, 10B, 14 created by the prong recesses 130, 131 which outer design may, for example, be conical. In addition, various sizes of the hollow passages may easily be achieved by using insert pins of various sizes.

If there is a need for further inlets/outlets along the tubular body of the cannula, further insert pins and prong recesses may be arranged in the mold along the cavity.

The mold 100 furthermore comprises at least one inlet passage 140 configured to allow the introduction of molding material in to the mold cavity 111. The inlet passage may be configured as a hole extending from the exterior of the mold to the cavity 111 to make it possible to deliver material under pressure to the cavity. In some embodiments, the inlet passage 140 may be positioned between the prong recesses 130, 131, but it could also be disposed in other positions.

After positioning the first and second inserts 114, 118, as well as the inserts pins 123, 126 in their respective molding positions, the mold 100 is filled with manufacturing material by introducing the manufacturing material into the mold 100 through the inlet passage 140 under pressure. The total time cycle for producing a cannula may be from about 10 seconds to about 1 minute.

The inner diameter of the tubular body 2 is suitably in the range of 2-4 mm, preferably about 3 mm, and thus, the first and second inserts 114, 118 used for providing the wall 7 in a desired position within the tubular body 2 suitably have an outer diameter in the range of 2-4 mm, preferably about 3 mm. The first and second inserts 114, 118 may also have different outer diameters, for example, the diameter of first insert 114 may be bigger, such as about 4 mm, while the diameter of second insert 118 may be smaller, such as about 2 mm.

The inner diameter of the hollow prongs 10, 10A, 10B, 14 is suitably about 1-2 mm, and thus, the insert pins 123, 126 used for providing the hollow space suitably have an outer diameter of 1-2 mm.

Depending on whether the cannula is intended to be used by adults, children or infants, different sizes of cannulae may be manufactured. In particular, the distance between the hollow prongs to be arranged in the nostrils (in FIGS. 1A and 1B, the hollow prongs denoted 10, 10B) may be varied. A suitable distance between the hollow prongs 10, 10B on a cannula for adults is about 15-17 mm, preferably 16 mm, a suitable distance between the hollow prongs 10, 10B on a cannula for children is 11-13 mm, preferably about 12 mm, and a suitable distance between the prongs 10, 10B on a cannula for infants is about 8-10 mm, preferably about 9 mm. In order to easily produce these three different variants of the cannula 1, three different variants of the cannula mold 100 may be provided.

Notably, the first and second inserts 114, 118 and first and second insert pins 123, 126 used during production may advantageously be identical for use in all three described variants of cannula mold 100.

The techniques described herein may also be modified to provide for the production of a cannula 1 which further comprises an oral breath collector 15, as shown in FIGS. 2A, 2B, 4A, and 4B. The manufacturing of an oral breath collector 15 may also be performed by injection molding. The oral breath collector 15 may be manufactured in different sizes, depending on whether the cannula system is intended for infants, children or adults.

In embodiments of the cannula comprising an oral breath collector 15, the cannula mold 100 for producing a cannula is shaped to include features for forming an additional inlet 8B comprising a hollow prong 14 molded integrally with the tubular body 2. The hollow space in the hollow prong 14 is created with a pin insert as described above.

The manufacturing of the nozzles 16, 17 may also be performed by injection molding. The manufacturing of the nozzles 16, 17 in accordance with FIGS. 1A and 1B will now be described in further detail with reference to FIG. 10.

A nozzle mold K for producing a nozzle 16, 17 is shaped to create a desired outer shape of the nozzle. Preferably, the nozzles 16, 17 are slightly curved and have an end portion with a reduced diameter configured to fit tightly into the first or second end portions 3, 4 of the tubular body 2 of the cannula 1 upon assembly of the cannula system 1A.

An elbowed cavity in a nozzle 16, 17 is provided by providing cavity tools L, M by the inlet and outlet portions of the nozzles 16, 17, and then moving them towards each other until they are located in a position which provides for the formation of an elbowed cavity in the nozzle 16, 17. The respective ends of the cavity tools L, M are designed to provide a tight seal against each other when reaching their final positions.

In order to provide for a user-friendly design of the cannula system 1A, that follows the contours of the face, and also to provide for an expedient channel for the flow of gases through the cannula system, the first nozzle 16 suitably has an elbowed cavity. The manufacturing processes disclosed herein present a very convenient and efficient way of providing an elbowed cavity, namely by the use of the two cavity tools L, M which are introduced into the nozzle from two different directions. The cavity tools L, M may thus be of a straight form, while the resulting cavity has an elbowed form. Elbowed cavities of different sizes may easily be created by a simple substitution of cavity tools.

The cavity tool M is suitably shaped to provide an end portion with a reduced diameter within the nozzle 16, 17, in order for an extension tube, such as a sampling tube or a treating gas tube, to be tightly fitted into the nozzle 16, 17 upon assembly of the cannula system 1A. The end portion with a reduced diameter is created by forming the cavity tool to have two different diameters, M1, M2 in its length direction, wherein (with reference to FIG. 10) M1 is greater than M2.

The first nozzle 16 is adapted for the transport of exhaled gases from the cannula, and is generally adapted for a gas flow of about 50 ml/min. The cavity tools M, L used for providing a first nozzle 16 are therefore generally cylindrical and has the following diameters in the cross-sections M1, M2, L1 marked in FIG. 10: M1 from 1.5-2.5 mm, preferably about 2 mm; M2 from 0.5-1.5 mm, preferably about 1 mm; and L1 from 1-2 mm, preferably about 1.5 mm.

The second nozzle 17 is adapted for the supplementation of a treating gas to the cannula 1, and is generally adapted for a gas flow of about 5 liters/min. The cavity tools M, L used for providing a second nozzle 17 are therefore generally cylindrical and has the following diameters in the cross-sections M1, M2, L1 marked in FIG. 10: M1 from about 2.5-3.5 mm, preferably about 3 mm; M2 from about 1.5-2.5 mm, preferably about 2 mm, and L1 from about 1.0-2.0 mm, preferably about 1.5 mm.

Figure 10:
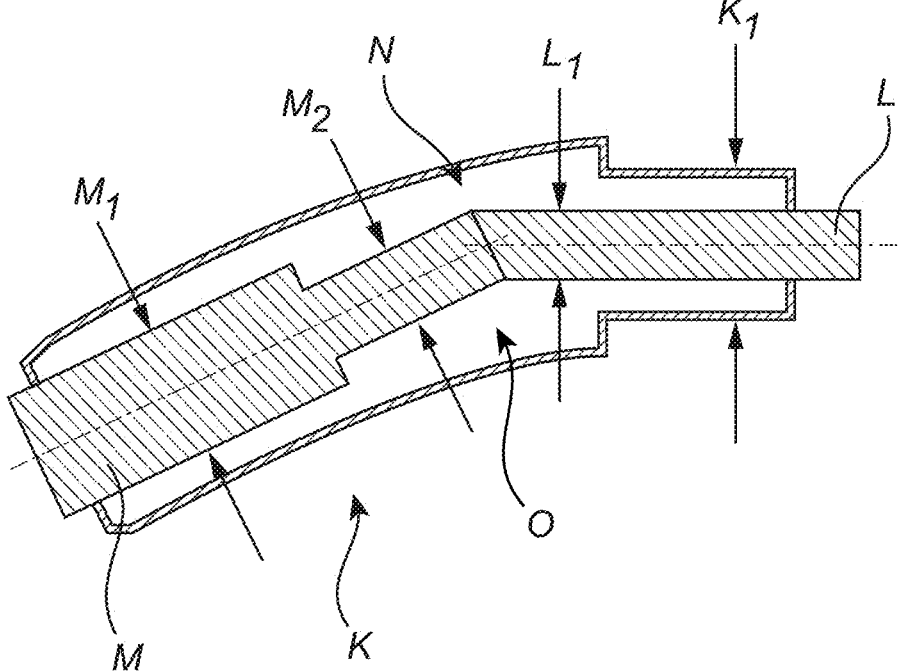
FIG. 10 shows cross-sectioned illustration of an example mold for manufacturing a nozzle configured for use with embodiments of cannulae herein disclosed, including cavity tools in their respective final positions.

The outer cross-sectional dimension of the nozzle 16, 17 at the end portion with a reduced diameter, marked as K1 in FIG. 10, is about 2-4 mm, preferably about 3 mm, that is, it essentially corresponds to the inner diameter of the tubular body 2, which is also about 2-4 mm, preferably about 3 mm.

The first nozzle 16 is generally connected via a sampling tube (not shown) to conventional analyzing means for analyzing at least one component (for example $CO_2$) of the exhaled gases. The sampling tube generally has an outer diameter of about 1.5-2.5 mm, preferably about 2 mm, and an inner diameter of about 0.5-1.5 mm, preferably about 1 mm. The outer diameter of the sampling tube essentially corresponds to the diameter of the cross-section M1 of the first nozzle 16, and thus the sampling tube fits tightly in the first nozzle 16.

The second nozzle 17 is generally connected via a treating gas tube (not shown) to a conventional supply of a treating gas (for example oxygen). The treating gas tube generally has an outer diameter of about 2.5-3.5 mm, preferably about 3 mm, and an inner diameter of about 1.5-2.5 mm, preferably about 2 mm. The outer diameter of the treating gas tube essentially corresponds to the diameter of the cross-section M1 of the second nozzle 17, and thus the treating gas tube fits tightly in the second nozzle 17.

In the step of assembling the nasal/oral cannula system 1A by solvent bonding, the desired components (for example cannula, nozzle(s) and/or extension tube(s)) are dipped in a suitable solvent, and then the components are mounted in the desired position. Depending on the intended use of the cannula system 1A, the components included may vary. The most general form of a cannula system 1A includes a cannula 1 and a first nozzle 16.

Exemplary solvents for use in solvent bonding of PVC are tetrahydrofuran and cyclohexanone, either used separately, or in combination. If used in combination, a suitable ratio is tetrahydrofuran mixed with cyclohexanone in a volume ratio of 2-8% to 92-98%, such as 5% to 95%, respectively.

The present disclosure is by no means limited to the preferred embodiments described above. On the contrary, many modifications and variations are possible within the scope of the appended claims. For example, although all the embodiments shown in the drawings comprise two nasal prongs, it is envisioned that a single prong could be sufficient, and that in embodiments where an oral breath collector is used for collection of exhaled gases, there need not even be any prongs (or corresponding inlets) at all. An inlet receiving exhaled gases from the patient's mouth via a scoop may thus constitute the only inlet into the subvolume 6A.

Turning now to FIGS. 11A-11C, a tool for injection molding of a nasal/oral cannula, such as that embodied in FIGS. 1A and 1B will now be described. FIG. 11A shows a cutaway perspective view of an embodiment of a tool for injection molding a cannula with the tool configured in a molding position. FIG. 11B shows the embodiment of the tool pictured in FIG. 11A transitioning from a closed, molding position to an open/release position. FIG. 11C shows the embodiment pictured in FIGS. 11A and 11B configured in an open/release position that allows the injection molded cannula to be removed from the mold. In each of FIGS. 11A-11C, a portion of the tool is cut away to better illustrate the interior or the tool where the mold as described above is arranged. The illustrated tool in the FIGS. 11A-11C is configured to manufacture two cannulae simultaneously; however, the principles disclosed may be modified to produce only a single cannula or more than two cannulae.

A tool 200, according to the present disclosure, is configured for use with embodiments of the mold described above. The tool 200 may comprise a tool body 201 formed by first and second tool body elements 202, 203. The first tool body element 202 may be a base, and the second tool body element 203 may be configured to be selectably coupled to a top surface of the first tool body element 202.

The first tool body element 202 is configured with a recess configured to receive and support the first mold body element 101. The second tool body element 203 is similarly configured with a recess configured in size and shape to support the second mold body element 102. The first and second tool mold body elements 202, 203 are configured so that when they are in the closed, molding position pictured in FIG. 11A, the two mold body elements 101, 102 are brought together to form interior cavity 111.

The recesses in the first and second tool mold body elements 202, 203 configured to receive the first and second mold body elements 101, 102 may, in some embodiments, further be configured to receive and work with different mold variations (for example, the molds configured to produce adult, child, and infant sized cannulae according to the dimensions and principles described above). This may achieved by configuring each mold so that the outer shape of each mold is the same, while only the interior cavity 111 varies.

Figure 9A:
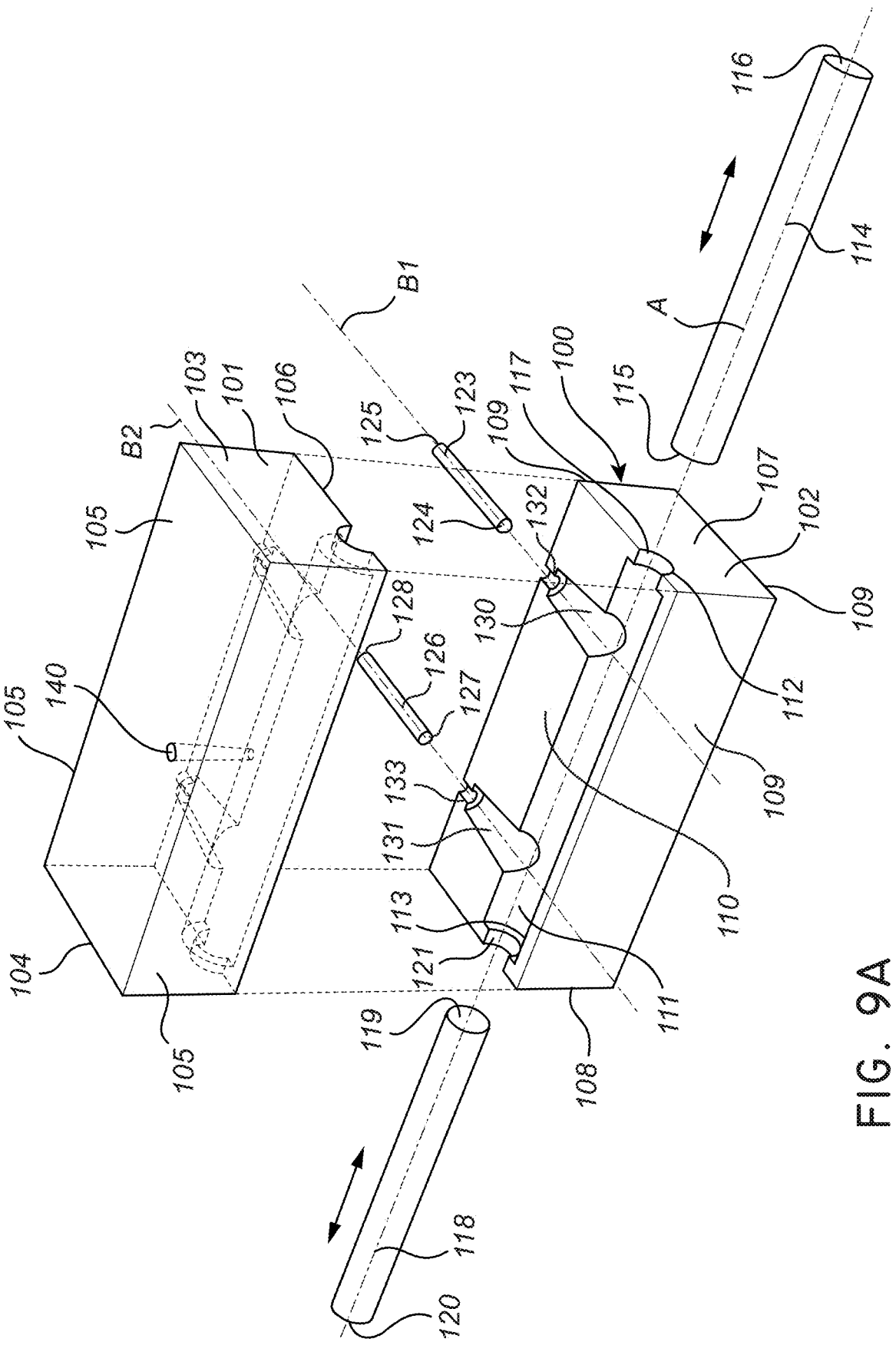
FIG. 9A shows an exploded view of a mold configured for use in the injection molding of a cannula according to the principles herein disclosed.
Figure 9B:
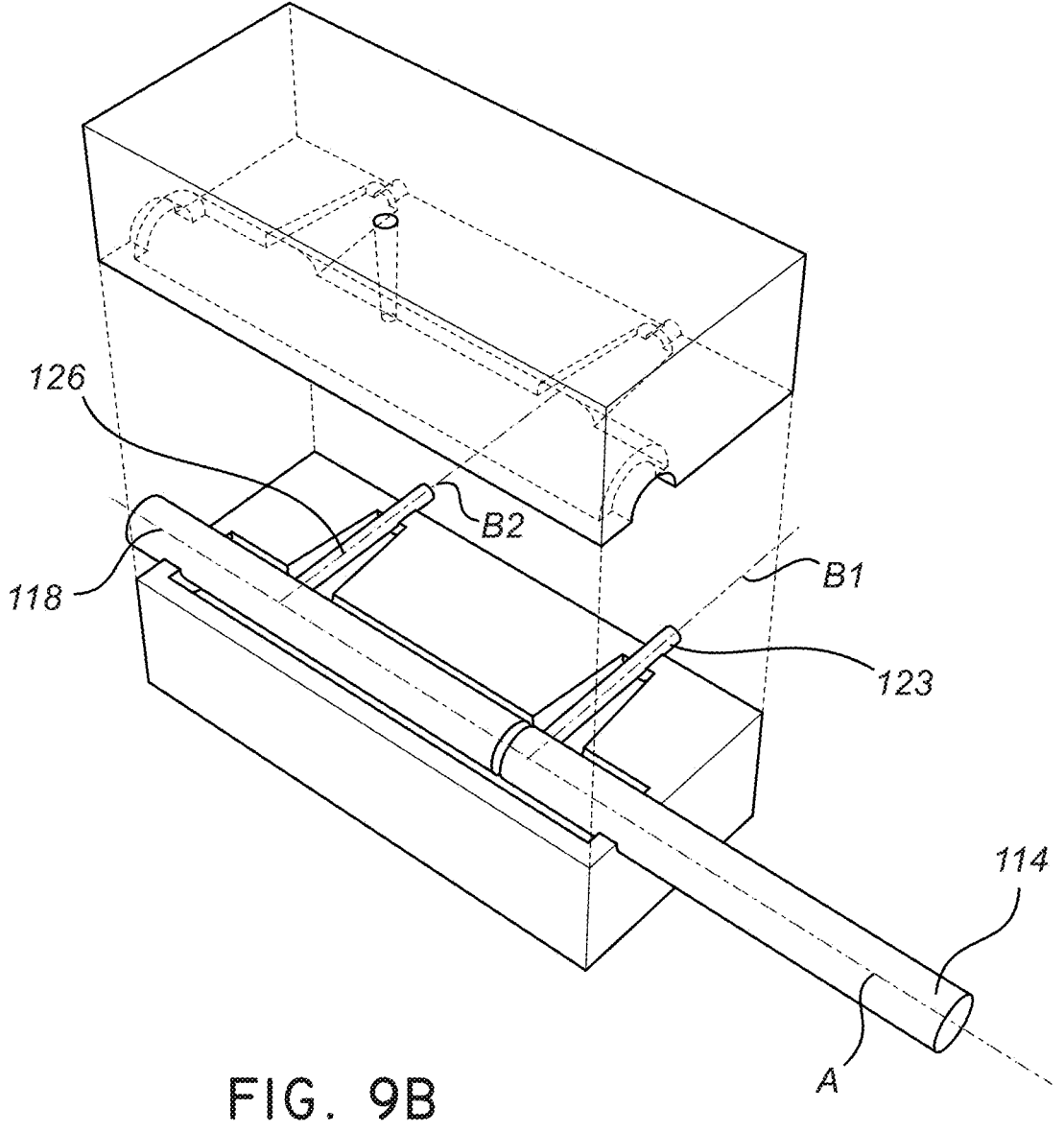
FIG. 9B shows a view of the embodiment of the mold depicted in FIG. 9A with inserts and pins disposed in a final molding position and with the mold cover removed.

Further, the first and second tool body elements 202, 203 are configured to provide a rigid support structure for the different components (for example, the inserts and pin inserts described in relation to FIGS. 9A-10) required to operate the mold 100 according to the principles herein disclosed.

The tool 200 may furthermore comprise a first device 204 arranged on one side of the mold 100. The first device 204 is configured to support the first insert 114 and arranged to move the first insert between its molding position (where it is inserted into the mold, as seen in FIG. 5B) and the retracted position (where the first insert is arranged outside the mold, as seen in FIG. 5A), or at least outside the cavity 111 so as to not interfere with the removal of the manufactured cannula. On the opposite side of the mold a second device 205 (as seen only in FIG. 11C), which is similar to the first device 204, configured to support the second insert 118.

The tool further comprises a third device 206 arranged along one of the elongated sides 105, 109 of the mold 100. The third device 206 is configured to support at least the first insert pin 123 and/or second insert pin 126, and move the first and/or second insert pins 123, 126 between the molding position and the retracted position where the insert pins 123, 126 are arranged outside the mold 100, or at least outside the prong recess so as to not interfere with removal of the manufactured cannula.

In some embodiments, the operation and movement of the tool as well as the supply/injection of molding material is controlled by a control unit, not shown, that is connected to all different components within the tool. Accordingly, the control unit monitors the operation of the first, the second and third devices 204, 205, 206, as well as the supply of molding material and removal of manufactured cannulae from the cavity of the mold. The control unit could be arranged on the tool body or remote from the tool. In some embodiments, the control unit may further comprise a computer running software configured to control and monitor the operation of the tool and direct the manufacturing processes described herein.

As previously described, the mold 100 and tool 200 according to the present disclosure make it possible to select and vary the position of the internal wall 7 within the cannula by controlling the position of the first and second inserts 114, 118 in the molding position. Positioning of the first and second inserts 114, 118 is controlled by the first and second devices 204, 205. In some embodiments, in order to minimize the complexity of the tool 200, the tool may be configured so that the first and second inserts 114, 118 are only movable between their molding and the release positions. And, in certain embodiments, the first and second inserts 114, 118 may be configured to move (by configuring the tool 200 and corresponding first and second device 204, 205) in response to the opening and closing of the tool 200. This operation will now be described with particular reference to FIG. 11B, which illustrates the motion of the various components as the tool 200 is moved from a closed, molding position to an open position.

In this embodiment of the tool 200, the first and second devices 204, 205 of the tool each comprise an elongated cylindrical recess 207 (as seen in FIG. 11B) extending coaxially with the longitudinal axis A of the mold (the longitudinal axis A can be seen in FIGS. 5A and 5B). The length of the recess may exceed the length of the first and second inserts 114, 118. The first and second inserts 114, 118 are inserted into the cylindrical recesses 207 and an insert locking device, not shown in the figures, may be provided to fix the inserts in place. In some embodiments the locking device may be a pin. In some embodiments, the locking device may be adjustable, so that the first and second inserts can be adjusted and locked into a plurality of selectable different positions. This may advantageously allow the tool and mold to work for the injection molding of cannulae with walls in different positions.

In another embodiment, the length of the first and second inserts 114, 118 is fixed to correspond to a desired longitudinal position of the wall in the manufactured cannula instead of adjusting the position in which the inserts are locked in the first and second device 204, 205. This embodiment may provide a reliable solution for producing a single type of cannulae with a single wall position that could be used over a long period of time without adjustment.

Insert pins 123, 126 are similarly disposed within recesses within third device 206. As long as the outside design and size of the mold 100 remains constant there is no need to adjust the position of the insert pins 123, 126 in the third device 206 along the axes B1 and B2. If adjustments are desired, the same solutions as described above in relation to the first and second inserts could also be used for the insert pins.

However, it should be noted that the third device 206 must be adapted to molds designed for cannulae of different sizes since the distance between the two hollow prongs may be varied. This could be achieved by supporting the insert pins in different longitudinal positions along axis A within the third device 206, thereby adapting the tool to molds intended for cannulae of different sizes. For example, third device 206 could provide a plurality of recesses spaced at intervals corresponding to the desired widths. Pin inserts can then be placed in the recesses corresponding to the desired width.

Returning now to a description of the movement of the first and second inserts 114, 118 and first and second insert pins 123, 126, in order to ensure that the movement of the first and second inserts 114, 118, as well as the insert pins 123, 126 is done properly, the tool 200 may be configured to first introduce the first and second inserts 114, 118 into the molding position within the cavity of the mold before the insert pins 123, 126 are moved into position. Accordingly, the illustrated tool 200 is configured such that the movement of the first and second tool body elements 202 and 203 between the molding and release positions mechanically generates the desired movement of the first second devices 204, 205 prior to the movement of the third device 206.

Referring specifically to FIG. 11B, this movement may be achieved with a first guide arm 210 secured in the second tool body element 203 and extending through a first guide passage 211 in the first device 204 such that when the first and second tool body element 202 and 203 are moved to the molding position, i.e. closed position, the first guide arm 210 will force the first device 204 and the first insert 114 into the mold achieving the molding position. Similarly, a second guide arm 212 and a second guide passage 213 are disposed on the opposite side of the mold 100 to generate the movement of the second device 205 between the molding and release position. The tool 200 furthermore comprises a third guide arm 214 secured in the second tool body element 203 and extending through a third guide passage 215 in the third device 206 to move the insert pins 123, 126 between the molding position and the release position.

After the molding is completed, the first and second tool body elements 202 and 203 are separated and the guide arms 210, 212 and 214 generate the desired movement of the first and second inserts and the insert pins to the release position and the manufactured cannula may be removed from the cavity 111 in the mold 100. Once the cannula is removed the mold and tool is ready for the next production cycle. This design advantageously reduces the number of components that need to be powered and controlled separately which reduces the overall cost for the tool and reduces the risk of malfunction and unintended interruptions in the production.

The desired movement of the first and second tool body elements 202, 203 may be generated by electrical engines or hydraulic cylinders (not shown) controlled by the control unit.

Additionally, variations to the disclosed embodiments can be understood and effected by the skilled person from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

Conditional language used herein, such as, among others, "can," "might," "may," "for example," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A respiratory cannula system comprising:
a treating gas tube configured to receive treating gas from a gas source;
a first nozzle configured to receive the treating gas from the treating gas tube;
a cannula comprising:
a tubular body comprising a first end, a second end opposite the first end, and an interior, said first end configured to connect to the first nozzle;
a wall arranged within the interior of the tubular body and configured to divide the interior of the tubular body into a first interior portion and a second interior portion, said first interior portion configured to receive said treating gas from the first nozzle;
an outlet extending through the tubular body and in fluid communication with the first interior portion;
a first nostril prong extending outward from the tubular body at the outlet and configured to direct said treating gas to a first nostril of a subject;
a first inlet extending through the tubular body and in fluid communication with the second interior portion;
a second nostril prong extending outward from the tubular body at the first inlet and configured to direct gases exhaled from a second nostril of the subject into said second interior portion; and
a second inlet extending through the tubular body and in fluid communication with the second interior portion, wherein said wall is integrally formed with the tubular body at the second inlet and is oriented perpendicular relative to an axis extending through a center of the tubular body;
an oral breath collector configured to connect to the tubular body at the second inlet and direct gases exhaled from a mouth of the subject into said second interior portion;
a second nozzle configured to connect to the second end of the tubular body and receive said gases exhaled from the subject's second nostril and mouth via said second interior portion; and
a sampling tube configured to receive said exhaled gases from the second nozzle and direct said exhaled gases to a gas analyzer.

2. The respiratory cannula system of claim 1, wherein the wall of the cannula is parallel to an axis extending through the second inlet of the cannula.

3. The respiratory cannula system of claim 1, wherein the cannula further comprises a third prong extending from the tubular body at the second inlet and configured to direct the gases exhaled from the subject's mouth to the second inlet, and wherein the oral breath collector is configured to connect to the third prong.

4. The respiratory cannula system of claim 3, wherein the oral breath collector comprises a curved body, a channel extending along a portion of the curved body, and an aperture at a top of the channel, and wherein the aperture is configured to receive a portion of the third prong of the cannula.

5. The respiratory cannula system of claim 1, wherein said tubular body further comprises a length L extending between the first and second ends, and wherein said second inlet is disposed at a distance of about L/2 from said first end.

6. A respiratory cannula system comprising:
a cannula comprising:
a tubular body comprising a first end, a second end opposite the first end, and an interior;
a wall configured to divide the interior of the tubular body into a first interior portion and a second interior portion, said first interior portion configured to receive treating gas;
an outlet extending through the tubular body and in fluid communication with the first interior portion;
a first nostril prong extending outward from the tubular body at the outlet and configured to direct said treating gas to a first nostril of a subject;
a first inlet extending through the tubular body and in fluid communication with the second interior portion;
a second inlet extending through the tubular body and in fluid communication with the second interior portion, wherein said wall is integrally formed with the tubular body at the second inlet; and
a second nostril prong extending outward from the tubular body at the first inlet and configured to direct gases exhaled from a second nostril of the subject into said second interior portion; and
an oral breath collector configured to connect to the tubular body at the second inlet and direct gases exhaled from a mouth of the subject into said second interior portion;
wherein said second interior portion is configured to direct said gases exhaled from the subject's second nostril and mouth towards the second end of the tubular body.

7. The respiratory cannula system of claim 6, wherein the wall of the cannula is parallel to an axis extending through the second inlet of the cannula.

8. The respiratory cannula system of claim 6, wherein the cannula further comprises a third prong extending from the tubular body at the second inlet and configured to direct the gases exhaled from the subject's mouth to the second inlet, and wherein the oral breath collector is configured to connect to the third prong.

9. The respiratory cannula system of claim 8, wherein the oral breath collector comprises a curved body, a channel extending along a portion of the curved body, and an aperture at a top of the channel, and wherein the aperture is configured to receive a portion of the third prong of the cannula.

10. The respiratory cannula system of claim 6, further comprising:
a treating gas tube configured to receive said treating gas from a gas source and provide said treating gas to said first interior portion; and a sampling tube configured to receive said gases exhaled from the subject's second nostril and mouth via said second interior portion and direct said exhaled gases to a gas analyzer.

11. The respiratory cannula system of claim 10, further comprising:

a first nozzle configured to connect the treating gas tube to the first end of the tubular body; and a second nozzle configured to connect the sampling tube to the second end of the tubular body.

12. The respiratory cannula system of claim 6, wherein said wall is oriented perpendicular relative to an axis extending through a center of the tubular body.

13. A respiratory cannula comprising:

a tubular body comprising a first end, a second end opposite the first end, and an interior;

a wall configured to divide the interior of the tubular body into a first interior portion and a second interior portion, said first interior portion configured to receive treating gas;

an outlet extending through the tubular body and in fluid communication with the first interior portion;

a first nostril prong extending outward from the tubular body at the outlet and configured to direct said treating gas to a first nostril of a subject;

a first inlet extending through the tubular body and in fluid communication with the second interior portion;

a second nostril prong extending outward from the tubular body at the first inlet and configured to direct gases exhaled from a second nostril of the subject into said second interior portion; and a second inlet extending through the tubular body and in fluid communication with the second interior portion, wherein said wall is integrally formed with the tubular body at the second inlet;

wherein the respiratory cannula is configured to connect to an oral breath collector at the second inlet of the tubular body, said second inlet configured to allow gases exhaled from a mouth of the subject to flow into said second interior portion;

wherein said second interior portion is configured to direct said gases exhaled from the subject's second nostril and mouth towards the second end of the tubular body.

14. The respiratory cannula of claim 13, wherein the wall is parallel to an axis extending through the second inlet.

15. The respiratory cannula of claim 13, wherein said second end is an exit port configured to allow the gases exhaled from the subject's second nostril and mouth to exit said second interior portion.

16. The respiratory cannula of claim 13, wherein said first end is an entrance port configured to allow the treating gas to enter said first interior portion.

17. The respiratory cannula of claim 13, wherein the second end is configured to connect to a second nozzle, said second nozzle configured to deliver the gases exhaled from the subject's second nostril and mouth to a sampling tube.

18. The respiratory cannula of claim 13, wherein the first end is configured to connect to a first nozzle, said first nozzle configured to deliver the treating gas to said first interior portion of the respiratory cannula.

19. The respiratory cannula of claim 13, wherein said tubular body further comprises a length L extending between the first and second ends, and wherein said second inlet is disposed at a distance of about L/2 from said first end.

20. The respiratory cannula of claim 13, further comprising a third prong extending from the tubular body at the second inlet and configured to direct the gases exhaled from the subject's mouth to the second inlet, and wherein the oral breath collector is configured to connect to the third prong.

* * * * *